(12) United States Patent
Inouye

(10) Patent No.: US 9,938,539 B2
(45) Date of Patent: Apr. 10, 2018

(54) METHOD FOR SYNTHETIC GENES

(71) Applicant: JNC CORPORATION, Tokyo (JP)

(72) Inventor: Satoshi Inouye, Kanagawa (JP)

(73) Assignee: JNC CORPORATION, Tokyo (JP)

( * ) Notice: Subject to any disclaimer, the term of this patent is extended or adjusted under 35 U.S.C. 154(b) by 0 days.

(21) Appl. No.: 14/848,535

(22) Filed: Sep. 9, 2015

(65) Prior Publication Data

US 2016/0076052 A1 Mar. 17, 2016

(30) Foreign Application Priority Data

Sep. 11, 2014 (JP) ................................ 2014-185629

(51) Int. Cl.
*C12N 15/85* (2006.01)
*C12N 9/02* (2006.01)

(52) U.S. Cl.
CPC ........... *C12N 15/85* (2013.01); *C12N 9/0069* (2013.01); *C12Y 113/12* (2013.01); *C12Y 113/12005* (2013.01); *C12Y 113/12007* (2013.01); *C12Y 113/12013* (2013.01); *C12N 2800/22* (2013.01)

(58) Field of Classification Search
CPC .................................................. C12N 2800/22
See application file for complete search history.

(56) References Cited

U.S. PATENT DOCUMENTS

| 6,232,107 | B1 * | 5/2001 | Bryan | ............... | A61K 47/48576 435/183 |
| 2005/0032730 | A1 * | 2/2005 | Von Der Mulbe | ..... | A61K 38/19 514/44 R |
| 2010/0035287 | A1 * | 2/2010 | Tannous | ................... | C12Q 1/66 435/8 |
| 2010/0093029 | A1 | 4/2010 | Coleman et al. | | |
| 2010/0273202 | A1 | 10/2010 | Inouye et al. | | |
| 2012/0028257 | A1 | 2/2012 | Jiang et al. | | |
| 2014/0242574 | A1 | 8/2014 | Inouye et al. | | |

FOREIGN PATENT DOCUMENTS

| JP | 2010-172260 A | 8/2010 | | |
| JP | 2014-193147 A | 10/2014 | | |
| WO | WO-0065076 A2 | 11/2000 | | |
| WO | WO-02/088168 A2 | 11/2002 | | |
| WO | WO 2011144216 A1 * | 11/2011 | ............... | C12Q 1/18 |
| WO | WO 2013143699 A1 * | 10/2013 | ............. | C12N 15/67 |

OTHER PUBLICATIONS

GB Application No. 1515662.3—Search Report dated Jun. 20, 2016.
International Search Report for PCT/EP00/03765, dated Mar. 8, 2001.
Satoshi Inouye, et al., "Protein expression of preferred human codon-optimized *Gaussia* luciferase genes with an artificial open-reading frame in mammalian and bacterial cells", Protein Expression and Purification, 2016, 28, pp. 93-100.
Japanese Office Action dated Dec. 22, 2017 issued in corresponding Japanese patent application No. 2014-185629 (12 pages) and its English-language translation thereof (9 pages).
Liu, Zhiguo et al., "Mammalian expression levels of cellulase and xylanase genes optimised by human codon usage are not necessarily higher than those optimised by the extremely biased approach," Biotechnol. Lett., Jun. 2014, vol. 36, pp. 2169-2176.
Branchini, Bruce. R. et al., "Red-emitting luciferases for bioluminescence reporter and imaging applications,"Analytical Biochemistry 396, (2010), pp. 290-297.
Kudla, Grzegorz et al., "High Guanine and Cytosine Content Increases mRNA Levels in Mammalian Cells," PLOS Biology, 2006,vol. 4, Issue 6, e180, pp. 0933-0942.
Satoshi Inouye, Yoshiyuki Sakaki, "'Aequorin', A Photoprotein of *Aequorea victoria*," Kagaku to Seibutsu, 1987 vol. Issue 4 pp. 224-232.
Vernon, W. I., et al., "Assay for Intracellular Calcium Using a Codon-Optimized Aequorin," BioTechniques, Oct. 2002, vol. 33, No. 4, pp. 730, 732, 734.
Zolotukhin, Sergei et al., "A "Humanized" Green Fluorescent Protein cDNA Adapted for High-Level Expression in Mammalian Cells," Journal of Virology, Jul. 1996, vol. 70, No. 7, pp. 4646-4654.
Zhang, Guohong, et al., "An Enhanced Green Fluorescent Protein Allows Sensitive Detection of Gene Transfer in Mammalian Cells." Biochemical and Biophysical Research Communications, 1996, vol. 227, pp. 707-711.
Cloning vector pEGFP-C1, complete sequence, enhanced green fluorescent protein (egfp) and neomycin phosphotransferase genes, complete cds, GeneBank accession No. U55763, Jun. 23, 2010 [retrieved on Dec. 20, 2017], Retrieved from the Internet, URL, https://www.ncbi.nlmnih.gov/nuccore/1377914?sat-4&satkey-42752653.
Mezzanotte, Laura et al., "Sensitive Dual Color In Vivo Bioluminescence Imaging Using a New Red Codon Optimized Firefly Luciferase and a Green Click Beetle Luciferase," PLOS one, 2011, vol. 6, No. 4, e19277, pp. 1-9.
Graf, Marcus et al., "Rationales of Gene Design and De Novo Gene Construction," Systems Biology and Synthetic Biology, 2009, pp. 411-438.
Ohmiya, Y. Bunseki (analysis), 2008,vol. 12, pp. 649-655.

* cited by examiner

*Primary Examiner* — Jennifer Dunston

(74) *Attorney, Agent, or Firm* — Drinker Biddle & Reath LLP

(57) ABSTRACT

The present invention provides a method of designing an optimized gene which comprises altering a nucleotide sequence of a target protein gene, so that only preferential codons with high frequency of use in human cells are selected and a GC content of not less than 60% is achieved. A gene design method which involves the feature "only preferential codons with high frequency of use are selected and a GC content of not less than 60% is achieved" can be established as a general rule for preparing proteins with high expression level, in order to obtain chemically synthesized genes for proteins capable of high-level expression in eukaryotes.

11 Claims, No Drawings

SEQUENCE LISTING

<160> NUMBER OF SEQ ID NOS: 23

<210> SEQ ID NO 1
<211> LENGTH: 570
<212> TYPE: DNA
<213> ORGANISM: Aequorea victoria
<220> FEATURE:
<221> NAME/KEY: CDS
<222> LOCATION: (1)..(567)

<400> SEQUENCE: 1

| | | | | | | | | | | | | | | | | |
|---|---|---|---|---|---|---|---|---|---|---|---|---|---|---|---|---|
| gtc | aag | ctt | aca | tca | gac | ttc | gac | aac | cca | aga | tgg | att | gga | cga | cac | 48 |
| Val | Lys | Leu | Thr | Ser | Asp | Phe | Asp | Asn | Pro | Arg | Trp | Ile | Gly | Arg | His | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| aag | cat | atg | ttc | aat | ttc | ctt | gat | gtc | aac | cac | aat | gga | aaa | atc | tct | 96 |
| Lys | His | Met | Phe | Asn | Phe | Leu | Asp | Val | Asn | His | Asn | Gly | Lys | Ile | Ser | |
| | | | 20 | | | | | 25 | | | | | 30 | | | |

| | | | | | | | | | | | | | | | | |
|---|---|---|---|---|---|---|---|---|---|---|---|---|---|---|---|---|
| ctt | gac | gag | atg | gtc | tac | aag | gca | tct | gat | att | gtc | atc | aat | aac | ctt | 144 |
| Leu | Asp | Glu | Met | Val | Tyr | Lys | Ala | Ser | Asp | Ile | Val | Ile | Asn | Asn | Leu | |
| | | 35 | | | | | 40 | | | | | 45 | | | | |

| | | | | | | | | | | | | | | | | |
|---|---|---|---|---|---|---|---|---|---|---|---|---|---|---|---|---|
| gga | gca | aca | cct | gag | caa | gcc | aaa | cga | cac | aaa | gat | gct | gta | gaa | gcc | 192 |
| Gly | Ala | Thr | Pro | Glu | Gln | Ala | Lys | Arg | His | Lys | Asp | Ala | Val | Glu | Ala | |
| 50 | | | | | 55 | | | | | 60 | | | | | | |

| | | | | | | | | | | | | | | | | |
|---|---|---|---|---|---|---|---|---|---|---|---|---|---|---|---|---|
| ttc | ttc | gga | gga | gct | gga | atg | aaa | tat | ggt | gtg | gaa | act | gat | tgg | cct | 240 |
| Phe | Phe | Gly | Gly | Ala | Gly | Met | Lys | Tyr | Gly | Val | Glu | Thr | Asp | Trp | Pro | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gca | tat | att | gaa | gga | tgg | aaa | aaa | ttg | gct | act | gat | gaa | ttg | gag | aaa | 288 |
| Ala | Tyr | Ile | Glu | Gly | Trp | Lys | Lys | Leu | Ala | Thr | Asp | Glu | Leu | Glu | Lys | |
| | | | | 85 | | | | | 90 | | | | | 95 | | |

| | | | | | | | | | | | | | | | | |
|---|---|---|---|---|---|---|---|---|---|---|---|---|---|---|---|---|
| tac | gcc | aaa | aac | gaa | cca | acg | ctc | atc | cgt | ata | tgg | ggt | gat | gct | ttg | 336 |
| Tyr | Ala | Lys | Asn | Glu | Pro | Thr | Leu | Ile | Arg | Ile | Trp | Gly | Asp | Ala | Leu | |
| | | | 100 | | | | | 105 | | | | | 110 | | | |

| | | | | | | | | | | | | | | | | |
|---|---|---|---|---|---|---|---|---|---|---|---|---|---|---|---|---|
| ttt | gat | atc | gtt | gac | aaa | gat | caa | aat | gga | gcc | att | aca | ctg | gat | gaa | 384 |
| Phe | Asp | Ile | Val | Asp | Lys | Asp | Gln | Asn | Gly | Ala | Ile | Thr | Leu | Asp | Glu | |
| | | | | 115 | | | | | 120 | | | | | 125 | | |

| | | | | | | | | | | | | | | | | |
|---|---|---|---|---|---|---|---|---|---|---|---|---|---|---|---|---|
| tgg | aaa | gca | tac | acc | aaa | gct | gct | ggt | atc | atc | caa | tca | tca | gaa | gat | 432 |
| Trp | Lys | Ala | Tyr | Thr | Lys | Ala | Ala | Gly | Ile | Ile | Gln | Ser | Ser | Glu | Asp | |
| | 130 | | | | | 135 | | | | | 140 | | | | | |

| | | | | | | | | | | | | | | | | |
|---|---|---|---|---|---|---|---|---|---|---|---|---|---|---|---|---|
| tgc | gag | gaa | aca | ttc | aga | gtg | tgc | gat | att | gat | gaa | agt | gga | caa | ctc | 480 |
| Cys | Glu | Glu | Thr | Phe | Arg | Val | Cys | Asp | Ile | Asp | Glu | Ser | Gly | Gln | Leu | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gat | gtt | gat | gag | atg | aca | aga | caa | cat | tta | gga | ttt | tgg | tac | acc | atg | 528 |
| Asp | Val | Asp | Glu | Met | Thr | Arg | Gln | His | Leu | Gly | Phe | Trp | Tyr | Thr | Met | |
| | | | | 165 | | | | | 170 | | | | | 175 | | |

| | | | | | | | | | | | | |
|---|---|---|---|---|---|---|---|---|---|---|---|---|
| gat | cct | gct | tgc | gaa | aag | ctc | tac | ggt | gga | gct | gtc | ccc | taa | 570 |
| Asp | Pro | Ala | Cys | Glu | Lys | Leu | Tyr | Gly | Gly | Ala | Val | Pro | | |
| | | 180 | | | | | 185 | | | | | | | |

<210> SEQ ID NO 2
<211> LENGTH: 570
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(567)
<223> OTHER INFORMATION: Aequorea victoria humanized type

<400> SEQUENCE: 2

| | | | | | | | | | | | | | | | | |
|---|---|---|---|---|---|---|---|---|---|---|---|---|---|---|---|---|
| gtg | aag | ctg | aca | tcc | gac | ttc | gac | aac | cca | aga | tgg | att | gga | cgc | cat | 48 |
| Val | Lys | Leu | Thr | Ser | Asp | Phe | Asp | Asn | Pro | Arg | Trp | Ile | Gly | Arg | His | |
| 1 | | | | 5 | | | | | 10 | | | | | 15 | | |

```
aag cac atg ttc aat ttc ctg gat gtg aac cac aat ggc aaa atc tct        96
Lys His Met Phe Asn Phe Leu Asp Val Asn His Asn Gly Lys Ile Ser
             20                  25                  30 ttg gac gag atg gtc tac aag gca tcc gat ata gtg atc aat aat ctt       144
Leu Asp Glu Met Val Tyr Lys Ala Ser Asp Ile Val Ile Asn Asn Leu
         35                  40                  45 ggg gca acc ccc gag cag gcc aaa cgg cac aag gat gct gtg gaa gcc       192
Gly Ala Thr Pro Glu Gln Ala Lys Arg His Lys Asp Ala Val Glu Ala
     50                  55                  60 ttt ttc ggc ggg gct ggg atg aag tat ggc gtg gaa act gac tgg cct       240
Phe Phe Gly Gly Ala Gly Met Lys Tyr Gly Val Glu Thr Asp Trp Pro
 65                  70                  75                  80 gca tat att gaa ggc tgg aaa aaa ctg gcc act gat gaa ctg gag aag       288
Ala Tyr Ile Glu Gly Trp Lys Lys Leu Ala Thr Asp Glu Leu Glu Lys
                 85                  90                  95 tat gcc aag aac gag cca acc ctc atc agg ata tgg ggt gat gcc ctc       336
Tyr Ala Lys Asn Glu Pro Thr Leu Ile Arg Ile Trp Gly Asp Ala Leu
            100                 105                 110 ttt gac atc gtt gac aag gac cag aac ggt gcc att acc ctg gat gag       384
Phe Asp Ile Val Asp Lys Asp Gln Asn Gly Ala Ile Thr Leu Asp Glu
        115                 120                 125 tgg aaa gca tac acc aag gct gcc ggt atc atc caa agc agc gaa gac       432
Trp Lys Ala Tyr Thr Lys Ala Ala Gly Ile Ile Gln Ser Ser Glu Asp
    130                 135                 140 tgt gag gaa aca ttc agg gtg tgc gat att gat gag agt ggg cag ctc       480
Cys Glu Glu Thr Phe Arg Val Cys Asp Ile Asp Glu Ser Gly Gln Leu
145                 150                 155                 160 gat gtt gat gag atg acc aga cag cat ctg gga ttt tgg tac aca atg       528
Asp Val Asp Glu Met Thr Arg Gln His Leu Gly Phe Trp Tyr Thr Met
                165                 170                 175 gac cct gcc tgc gag aaa ttg tac gga gga gct gtc ccc taa               570
Asp Pro Ala Cys Glu Lys Leu Tyr Gly Gly Ala Val Pro
            180                 185

<210> SEQ ID NO 3
<211> LENGTH: 570
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(567)
<223> OTHER INFORMATION: Aequorea victoria optimized type

<400> SEQUENCE: 3 gtc aag ctg acc agc gac ttc gac aac ccc aga tgg atc ggc aga cac        48
Val Lys Leu Thr Ser Asp Phe Asp Asn Pro Arg Trp Ile Gly Arg His
 1               5                  10                  15 aag cac atg ttc aac ttc ctg gac gtc aac cac aac ggc aag atc agc        96
Lys His Met Phe Asn Phe Leu Asp Val Asn His Asn Gly Lys Ile Ser
             20                  25                  30 ctg gac gag atg gtc tac aag gcc agc gac atc gtc atc aat aac ctg       144
Leu Asp Glu Met Val Tyr Lys Ala Ser Asp Ile Val Ile Asn Asn Leu
         35                  40                  45 ggc gcc acc ccc gag cag gcc aag aga cac aag gac gcc gtc gag gcc       192
Gly Ala Thr Pro Glu Gln Ala Lys Arg His Lys Asp Ala Val Glu Ala
     50                  55                  60 ttc ttc ggc ggc gcc ggc atg aag tac ggc gtc gag acc gac tgg ccc       240
Phe Phe Gly Gly Ala Gly Met Lys Tyr Gly Val Glu Thr Asp Trp Pro
 65                  70                  75                  80 gcc tac atc gag ggc tgg aag aag ctg gcc acc gat gag ctg gag aag       288
Ala Tyr Ile Glu Gly Trp Lys Lys Leu Ala Thr Asp Glu Leu Glu Lys
```

-continued

```
              Ala Tyr Ile Glu Gly Trp Lys Lys Leu Ala Thr Asp Glu Leu Glu Lys
                              85                  90                  95 tac gcc aag aac gag ccc acc ctg atc aga atc tgg ggc gac gcc ctg        336
Tyr Ala Lys Asn Glu Pro Thr Leu Ile Arg Ile Trp Gly Asp Ala Leu
            100                 105                 110 ttc gac atc gtg gac aag gac cag aac ggc gcc atc acc ctg gac gag        384
Phe Asp Ile Val Asp Lys Asp Gln Asn Gly Ala Ile Thr Leu Asp Glu
        115                 120                 125 tgg aag gcc tac acc aag gcc gcc ggc atc atc cag agc agc gag gac        432
Trp Lys Ala Tyr Thr Lys Ala Ala Gly Ile Ile Gln Ser Ser Glu Asp
    130                 135                 140 tgc gag gag acc ttc aga gtc tgc gac atc gat gag agc ggc cag ctg        480
Cys Glu Glu Thr Phe Arg Val Cys Asp Ile Asp Glu Ser Gly Gln Leu
145                 150                 155                 160 gac gtg gac gag atg acc aga cag cac ctg ggc ttc tgg tac aca atg        528
Asp Val Asp Glu Met Thr Arg Gln His Leu Gly Phe Trp Tyr Thr Met
                165                 170                 175 gac ccc gcc tgc gag aag ctg tac ggc ggc gcc gtc ccc taa                570
Asp Pro Ala Cys Glu Lys Leu Tyr Gly Gly Ala Val Pro
            180                 185

<210> SEQ ID NO 4
<211> LENGTH: 570
<212> TYPE: DNA
<213> ORGANISM: Clytia gregaria
<220> FEATURE:
<221> NAME/KEY: CDS
<222> LOCATION: (1)..(567)

<400> SEQUENCE: 4 gtc aaa ctc gat cct gat ttt gca aat cca aaa tgg atc aac aga cac         48
Val Lys Leu Asp Pro Asp Phe Ala Asn Pro Lys Trp Ile Asn Arg His
1               5                  10                  15 aaa ttt atg ttc aac ttt ttg gac ata aac ggt aat ggg aaa atc aca         96
Lys Phe Met Phe Asn Phe Leu Asp Ile Asn Gly Asn Gly Lys Ile Thr
            20                  25                  30 tta gat gaa atc gtc tcc aaa gct tca gac gac att tgt gct aaa ctg        144
Leu Asp Glu Ile Val Ser Lys Ala Ser Asp Asp Ile Cys Ala Lys Leu
        35                  40                  45 gat gca aca cca gaa cag acc aaa cgt cac cag gat gct gtt gaa gcg        192
Asp Ala Thr Pro Glu Gln Thr Lys Arg His Gln Asp Ala Val Glu Ala
    50                  55                  60 ttt ttc aag aaa atg ggc atg gat tat ggt aaa gaa gtt gca ttc cca        240
Phe Phe Lys Lys Met Gly Met Asp Tyr Gly Lys Glu Val Ala Phe Pro
65                  70                  75                  80 gaa ttt att aag gga tgg gaa gag ttg gcc gaa cac gac ttg gaa ctc        288
Glu Phe Ile Lys Gly Trp Glu Glu Leu Ala Glu His Asp Leu Glu Leu
                85                  90                  95 tgg tct caa aac aaa agt aca ttg atc cgt gaa tgg gga gat gct gtt        336
Trp Ser Gln Asn Lys Ser Thr Leu Ile Arg Glu Trp Gly Asp Ala Val
            100                 105                 110 ttc gac att ttc gac aaa gac gca agt ggc tca atc agt tta gac gaa        384
Phe Asp Ile Phe Asp Lys Asp Ala Ser Gly Ser Ile Ser Leu Asp Glu
        115                 120                 125 tgg aag gct tac gga cga atc tct gga atc tgt cca tca gac gaa gac        432
Trp Lys Ala Tyr Gly Arg Ile Ser Gly Ile Cys Pro Ser Asp Glu Asp
    130                 135                 140 gct gag aag acg ttc aaa cat tgt gat ttg gac aac agt ggc aaa ctt        480
Ala Glu Lys Thr Phe Lys His Cys Asp Leu Asp Asn Ser Gly Lys Leu
145                 150                 155                 160 gat gtt gat gag atg acc agg caa cat tta ggc ttc tgg tac aca ttg        528
```

|   |   |   |   |   |   |   |   |   |   |   |   | | |
|---|---|---|---|---|---|---|---|---|---|---|---|---|---|
| Asp | Val | Asp | Glu | Met | Thr | Arg | Gln | His | Leu | Gly | Phe | Trp | Tyr | Thr | Leu |
|   |   |   |   | 165 |   |   |   | 170 |   |   |   |   | 175 |   |   | gat cca act tct gat ggt ctt tat ggc aat ttt gtt ccc taa     570
Asp Pro Thr Ser Asp Gly Leu Tyr Gly Asn Phe Val Pro
             180                    185

<210> SEQ ID NO 5
<211> LENGTH: 570
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(567)
<223> OTHER INFORMATION: Clytia gregaria optimized type

<400> SEQUENCE: 5 gtg aag ctg gac ccc gac ttc gcc aac ccc aag tgg atc aac aga cac     48
Val Lys Leu Asp Pro Asp Phe Ala Asn Pro Lys Trp Ile Asn Arg His
1               5                 10                 15 aag ttc atg ttc aac ttc ctg gac atc aac ggc aac ggc aag atc acc     96
Lys Phe Met Phe Asn Phe Leu Asp Ile Asn Gly Asn Gly Lys Ile Thr
               20                 25                 30 ctg gac gag atc gtg agc aag gcc agc gac gac atc tgc gcc aag ctg     144
Leu Asp Glu Ile Val Ser Lys Ala Ser Asp Asp Ile Cys Ala Lys Leu
          35                 40                 45 gac gcc acc ccc gag cag acc aag aga cac cag gac gcc gtg gag gcc     192
Asp Ala Thr Pro Glu Gln Thr Lys Arg His Gln Asp Ala Val Glu Ala
50              55                 60 ttc ttc aag aag atg ggc atg gac tac ggc aag gag gtg gcc ttc ccc     240
Phe Phe Lys Lys Met Gly Met Asp Tyr Gly Lys Glu Val Ala Phe Pro
65              70                 75                 80 gag ttc atc aag ggc tgg gag gag ctg gcc gag cac gac ctg gag ctg     288
Glu Phe Ile Lys Gly Trp Glu Glu Leu Ala Glu His Asp Leu Glu Leu
               85                 90                 95 tgg agc cag aac aag agc acc ctg atc aga gag tgg ggc gac gcc gtg     336
Trp Ser Gln Asn Lys Ser Thr Leu Ile Arg Glu Trp Gly Asp Ala Val
               100               105               110 ttc gac atc ttc gac aag gac gcc agc ggc agc atc agc ctg gac gag     384
Phe Asp Ile Phe Asp Lys Asp Ala Ser Gly Ser Ile Ser Leu Asp Glu
          115               120               125 tgg aag gcc tac ggc aga atc agc ggc atc tgc ccc agc gac gag gac     432
Trp Lys Ala Tyr Gly Arg Ile Ser Gly Ile Cys Pro Ser Asp Glu Asp
130            135               140 gcc gag aag acc ttc aag cac tgc gac ctg gac aac agc ggc aag ctg     480
Ala Glu Lys Thr Phe Lys His Cys Asp Leu Asp Asn Ser Gly Lys Leu
145            150               155               160 gac gtg gac gag atg acc aga cag cac ctg ggc ttc tgg tac acc ctg     528
Asp Val Asp Glu Met Thr Arg Gln His Leu Gly Phe Trp Tyr Thr Leu
               165               170               175 gac ccc acc agc gac ggc ctg tac ggc aac ttc gtc ccc taa     570
Asp Pro Thr Ser Asp Gly Leu Tyr Gly Asn Phe Val Pro
             180                    185

<210> SEQ ID NO 6
<211> LENGTH: 558
<212> TYPE: DNA
<213> ORGANISM: Gaussia princeps
<220> FEATURE:
<221> NAME/KEY: CDS
<222> LOCATION: (1)..(555)

<400> SEQUENCE: 6

```
atg gga gtg aaa gtt ctt ttt gcc ctt att tgt att gct gtg gcc gag        48
Met Gly Val Lys Val Leu Phe Ala Leu Ile Cys Ile Ala Val Ala Glu
1               5                   10                  15 gcc aaa cca act gaa aac aat gaa gat ttc aac att gta gct gta gct        96
Ala Lys Pro Thr Glu Asn Asn Glu Asp Phe Asn Ile Val Ala Val Ala
                20                  25                  30 agc aac ttt gct aca acg gat ctc gat gct gac cgt ggt aaa ttg ccc       144
Ser Asn Phe Ala Thr Thr Asp Leu Asp Ala Asp Arg Gly Lys Leu Pro
            35                  40                  45 gga aaa aaa tta cca ctt gag gta ctc aaa gaa atg gaa gcc aat gct       192
Gly Lys Lys Leu Pro Leu Glu Val Leu Lys Glu Met Glu Ala Asn Ala
        50                  55                  60 agg aaa gct ggc tgc act agg gga tgt ctg ata tgc ctg tca cac atc       240
Arg Lys Ala Gly Cys Thr Arg Gly Cys Leu Ile Cys Leu Ser His Ile
65                  70                  75                  80 aag tgt aca ccc aaa atg aag aag ttt atc cca gga aga tgc cac acc       288
Lys Cys Thr Pro Lys Met Lys Lys Phe Ile Pro Gly Arg Cys His Thr
                85                  90                  95 tat gaa gga gac aaa gaa agt gca cag gga gga ata gga gag gct att       336
Tyr Glu Gly Asp Lys Glu Ser Ala Gln Gly Gly Ile Gly Glu Ala Ile
            100                 105                 110 gtt gac att cct gaa att cct ggg ttt aag gat ttg gaa ccc atg gaa       384
Val Asp Ile Pro Glu Ile Pro Gly Phe Lys Asp Leu Glu Pro Met Glu
        115                 120                 125 caa ttc att gca caa gtt gac cta tgt gta gac tgc aca act gga tgc       432
Gln Phe Ile Ala Gln Val Asp Leu Cys Val Asp Cys Thr Thr Gly Cys
130                 135                 140 ctc aaa ggt ctt gcc aat gtg caa tgt tct gat tta ctc aag aaa tgg       480
Leu Lys Gly Leu Ala Asn Val Gln Cys Ser Asp Leu Leu Lys Lys Trp
145                 150                 155                 160 ctg cca caa aga tgt gca act ttt gct agc aaa att caa ggc caa gtg       528
Leu Pro Gln Arg Cys Ala Thr Phe Ala Ser Lys Ile Gln Gly Gln Val
                165                 170                 175 gac aaa ata aag ggt gcc ggt ggt gat taa                               558
Asp Lys Ile Lys Gly Ala Gly Gly Asp
            180                 185

<210> SEQ ID NO 7
<211> LENGTH: 558
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(555)
<223> OTHER INFORMATION: Gaussia princeps humanized type

<400> SEQUENCE: 7 atg gga gtc aaa gtt ctg ttt gcc ctg atc tgc atc gct gtg gcc gag        48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc        96
Ala Lys Pro Thr Glu Asn Asn Glu Asp Phe Asn Ile Val Ala Val Ala
                20                  25                  30 agc aac ttc gcg acc acg gat ctc gat gct gac cgc ggg aag ttg ccc       144
Ser Asn Phe Ala Thr Thr Asp Leu Asp Ala Asp Arg Gly Lys Leu Pro
            35                  40                  45 ggc aag aag ctg ccg ctg gag gtg ctc aaa gag atg gaa gcc aat gcc       192
Gly Lys Lys Leu Pro Leu Glu Val Leu Lys Glu Met Glu Ala Asn Ala
        50                  55                  60
```

```
cgg aaa gct ggc tgc acc agg ggc tgt ctg atc tgc ctg tcc cac atc      240
Arg Lys Ala Gly Cys Thr Arg Gly Cys Leu Ile Cys Leu Ser His Ile
 65                  70                  75                  80 aag tgc acg ccc aag atg aag aag ttc atc cca gga cgc tgc cac acc      288
Lys Cys Thr Pro Lys Met Lys Lys Phe Ile Pro Gly Arg Cys His Thr
                 85                  90                  95 tac gaa ggc gac aaa gag tcc gca cag ggc ggc ata ggc gag gcg atc      336
Tyr Glu Gly Asp Lys Glu Ser Ala Gln Gly Gly Ile Gly Glu Ala Ile
                100                 105                 110 gtc gac att cct gag att cct ggg ttc aag gac ttg gag ccc atg gag      384
Val Asp Ile Pro Glu Ile Pro Gly Phe Lys Asp Leu Glu Pro Met Glu
            115                 120                 125 cag ttc atc gca cag gtc gat ctg tgt gtg gac tgc aca act ggc tgc      432
Gln Phe Ile Ala Gln Val Asp Leu Cys Val Asp Cys Thr Thr Gly Cys
        130                 135                 140 ctc aaa ggg ctt gcc aac gtg cag tgt tct gac ctg ctc aag aag tgg      480
Leu Lys Gly Leu Ala Asn Val Gln Cys Ser Asp Leu Leu Lys Lys Trp
145                 150                 155                 160 ctg ccg caa cgc tgt gcg acc ttt gcc agc aag atc cag ggc cag gtg      528
Leu Pro Gln Arg Cys Ala Thr Phe Ala Ser Lys Ile Gln Gly Gln Val
                165                 170                 175 gac aag atc aag ggg gcc ggt ggt gac taa                              558
Asp Lys Ile Lys Gly Ala Gly Gly Asp
                180                 185

<210> SEQ ID NO 8
<211> LENGTH: 558
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(555)
<223> OTHER INFORMATION: Gaussia princeps optimized type

<400> SEQUENCE: 8 atg ggc gtc aag gtc ctg ttc gcc ctg atc tgc atc gcc gtc gcc gag       48
Met Gly Val Lys Val Leu Phe Ala Leu Ile Cys Ile Ala Val Ala Glu
  1               5                  10                  15 gcc aag ccc acc gag aac aac gag gac ttc aac atc gtc gcc gtc gcc       96
Ala Lys Pro Thr Glu Asn Asn Glu Asp Phe Asn Ile Val Ala Val Ala
                 20                  25                  30 agc aac ttc gcc acc acc gac ctg gac gct gac aga ggc aag ctg ccc      144
Ser Asn Phe Ala Thr Thr Asp Leu Asp Ala Asp Arg Gly Lys Leu Pro
             35                  40                  45 ggc aag aag ctg ccc ctg gag gtc ctg aag gag atg gag gcc aac gcc      192
Gly Lys Lys Leu Pro Leu Glu Val Leu Lys Glu Met Glu Ala Asn Ala
         50                  55                  60 aga aag gcc ggc tgc acc aga ggc tgc ctg atc tgc ctg agc cac atc      240
Arg Lys Ala Gly Cys Thr Arg Gly Cys Leu Ile Cys Leu Ser His Ile
 65                  70                  75                  80 aag tgc acc ccc aag atg aag aag ttc atc ccc ggt aga tgc cac acc      288
Lys Cys Thr Pro Lys Met Lys Lys Phe Ile Pro Gly Arg Cys His Thr
                 85                  90                  95 tac gag ggc gac aag gag agc gcc cag ggc ggc atc ggc gag gcc atc      336
Tyr Glu Gly Asp Lys Glu Ser Ala Gln Gly Gly Ile Gly Glu Ala Ile
                100                 105                 110 gtc gac atc ccc gag atc ccc ggc ttc aag gac ctg gag ccc atg gag      384
Val Asp Ile Pro Glu Ile Pro Gly Phe Lys Asp Leu Glu Pro Met Glu
            115                 120                 125 cag ttc atc gcc cag gtc gac ctg tgc gtc gac tgc acc acc ggc tgc      432
Gln Phe Ile Ala Gln Val Asp Leu Cys Val Asp Cys Thr Thr Gly Cys
```

```
Gln Phe Ile Ala Gln Val Asp Leu Cys Val Asp Cys Thr Thr Gly Cys
        130                 135                 140 ctg aag ggc ctg gcc aac gtc cag tgc agt gac ctg ctg aag aag tgg      480
Leu Lys Gly Leu Ala Asn Val Gln Cys Ser Asp Leu Leu Lys Lys Trp
145                 150                 155                 160 ctg ccc cag aga tgc gcc acc ttc gcc agc aag atc cag ggc cag gtc      528
Leu Pro Gln Arg Cys Ala Thr Phe Ala Ser Lys Ile Gln Gly Gln Val
                165                 170                 175 gac aag atc aag ggc gcc ggc ggc gac taa                              558
Asp Lys Ile Lys Gly Ala Gly Gly Asp
                180                 185

<210> SEQ ID NO 9
<211> LENGTH: 510
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(507)
<223> OTHER INFORMATION: Oplophorus gracilirostris mutated 19 kDa
      protein humanized type

<400> SEQUENCE: 9 ttc aca ctc gaa gat ttc gtt ggg gac tgg cga cag aca gcc ggc tac       48
Phe Thr Leu Glu Asp Phe Val Gly Asp Trp Arg Gln Thr Ala Gly Tyr
1               5                   10                  15 aac ctg gac caa gtc ctt gaa cag gga ggt gtg tcc agt ttg ttt cag       96
Asn Leu Asp Gln Val Leu Glu Gln Gly Gly Val Ser Ser Leu Phe Gln
                20                  25                  30 aat ctc ggg gtg tcc gta act ccg atc caa agg att gtc ctg agc ggt      144
Asn Leu Gly Val Ser Val Thr Pro Ile Gln Arg Ile Val Leu Ser Gly
            35                  40                  45 gaa aat ggg ctg aag atc gac atc cat gtc atc atc ccg tat gaa ggt      192
Glu Asn Gly Leu Lys Ile Asp Ile His Val Ile Ile Pro Tyr Glu Gly
        50                  55                  60 ctg agc ggc gac caa atg ggc cag atc gaa aaa att ttt aag gtg gtg      240
Leu Ser Gly Asp Gln Met Gly Gln Ile Glu Lys Ile Phe Lys Val Val
65                  70                  75                  80 tac cct gtg gat gat cat cac ttt aag gtg atc ctg cac tat ggc aca      288
Tyr Pro Val Asp Asp His His Phe Lys Val Ile Leu His Tyr Gly Thr
                85                  90                  95 ctg gta atc gac ggg gtt acg ccg aac atg atc gac tat ttc gga cgg      336
Leu Val Ile Asp Gly Val Thr Pro Asn Met Ile Asp Tyr Phe Gly Arg
            100                 105                 110 ccg tat gaa ggc atc gcc gtg ttc gac ggc aaa aag atc act gta aca      384
Pro Tyr Glu Gly Ile Ala Val Phe Asp Gly Lys Lys Ile Thr Val Thr
        115                 120                 125 ggg acc ctg tgg aac ggc aac aaa att atc gac gag cgc ctg atc aac      432
Gly Thr Leu Trp Asn Gly Asn Lys Ile Ile Asp Glu Arg Leu Ile Asn
130                 135                 140 ccc gac ggc tcc ctg ctg ttc cga gta acc atc aac gga gtg acc ggc      480
Pro Asp Gly Ser Leu Leu Phe Arg Val Thr Ile Asn Gly Val Thr Gly
145                 150                 155                 160 tgg cgg ctg tgc gaa cgc att ctg gcg taa                              510
Trp Arg Leu Cys Glu Arg Ile Leu Ala
                165

<210> SEQ ID NO 10
<211> LENGTH: 510
<212> TYPE: DNA
<213> ORGANISM: Artificial sequence
```

```
<220> FEATURE:
<223> OTHER INFORMATION: synthetic DNA
<220> FEATURE:
<221> NAME/KEY: CDS
<222> LOCATION: (1)..(507)
<223> OTHER INFORMATION: Oplophorus gracilirostris mutated 19 kDa
      protein optimized type

<400> SEQUENCE: 10 ttc acc ctg gag gac ttc gtc ggc gac tgg aga cag acc gcc ggc tac      48
Phe Thr Leu Glu Asp Phe Val Gly Asp Trp Arg Gln Thr Ala Gly Tyr
1               5                   10                  15 aac ctg gac cag gtc ctg gag cag ggc ggc gtc agc agc ctg ttc cag      96
Asn Leu Asp Gln Val Leu Glu Gln Gly Gly Val Ser Ser Leu Phe Gln
            20                  25                  30 aac ctg ggc gtc agc gtc acc ccc atc cag aga atc gtc ctt agc ggc     144
Asn Leu Gly Val Ser Val Thr Pro Ile Gln Arg Ile Val Leu Ser Gly
        35                  40                  45 gag aac ggc ctg aag atc gac atc cac gtc atc atc ccc tac gag ggc     192
Glu Asn Gly Leu Lys Ile Asp Ile His Val Ile Ile Pro Tyr Glu Gly
    50                  55                  60 ctg agc ggc gac cag atg ggc cag atc gag aag atc ttc aag gtc gtc     240
Leu Ser Gly Asp Gln Met Gly Gln Ile Glu Lys Ile Phe Lys Val Val
65                  70                  75                  80 tac ccc gtc gac gac cac cac ttc aag gtc atc ctg cac tac ggc acc     288
Tyr Pro Val Asp Asp His His Phe Lys Val Ile Leu His Tyr Gly Thr
                85                  90                  95 ctg gtc atc gac ggc gtc acc ccc aac atg atc gac tac ttc ggt aga     336
Leu Val Ile Asp Gly Val Thr Pro Asn Met Ile Asp Tyr Phe Gly Arg
            100                 105                 110 ccc tac gag ggc atc gcc gtc ttc gac ggc aag aag atc acc gtc acc     384
Pro Tyr Glu Gly Ile Ala Val Phe Asp Gly Lys Lys Ile Thr Val Thr
        115                 120                 125 ggc acc ctg tgg aac ggc aac aag atc atc gac gag aga ctg atc aac     432
Gly Thr Leu Trp Asn Gly Asn Lys Ile Ile Asp Glu Arg Leu Ile Asn
    130                 135                 140 ccc gac ggc agc ctg ctg ttc aga gtc acc atc aac ggc gtc acc ggc     480
Pro Asp Gly Ser Leu Leu Phe Arg Val Thr Ile Asn Gly Val Thr Gly
145                 150                 155                 160 tgg aga ctg tgc gag aga atc ctg gcc taa                             510
Trp Arg Leu Cys Glu Arg Ile Leu Ala
                165

<210> SEQ ID NO 11
<211> LENGTH: 1653
<212> TYPE: DNA
<213> ORGANISM: Photinus pyralis
<220> FEATURE:
<221> NAME/KEY: CDS
<222> LOCATION: (1)..(1650)

<400> SEQUENCE: 11 atg gaa gac gcc aaa aac ata aag aaa ggc ccg gcg cca ttc tat cct      48
Met Glu Asp Ala Lys Asn Ile Lys Lys Gly Pro Ala Pro Phe Tyr Pro
1               5                   10                  15 cta gag gat gga acc gct gga gag caa ctg cat aag gct atg aag aga      96
Leu Glu Asp Gly Thr Ala Gly Glu Gln Leu His Lys Ala Met Lys Arg
            20                  25                  30 tac gcc ctg gtt cct gga aca att gct ttt aca gat gca cat atc gag     144
Tyr Ala Leu Val Pro Gly Thr Ile Ala Phe Thr Asp Ala His Ile Glu
        35                  40                  45 gtg aac atc acg tac gcg gaa tac ttc gaa atg tcc gtt cgg ttg gca     192
Val Asn Ile Thr Tyr Ala Glu Tyr Phe Glu Met Ser Val Arg Leu Ala
```

```
              50                  55                  60
gaa gct atg aaa cga tat ggg ctg aat aca aat cac aga atc gtc gta    240
Glu Ala Met Lys Arg Tyr Gly Leu Asn Thr Asn His Arg Ile Val Val
 65                  70                  75                  80 tgc agt gaa aac tct ctt caa ttc ttt atg ccg gtg ttg ggc gcg tta    288
Cys Ser Glu Asn Ser Leu Gln Phe Phe Met Pro Val Leu Gly Ala Leu
                     85                  90                  95 ttt atc gga gtt gca gtt gcg ccc gcg aac gac att tat aat gaa cgt    336
Phe Ile Gly Val Ala Val Ala Pro Ala Asn Asp Ile Tyr Asn Glu Arg
                100                 105                 110 gaa ttg ctc aac agt atg aac att tcg cag cct acc gta gtg ttt gtt    384
Glu Leu Leu Asn Ser Met Asn Ile Ser Gln Pro Thr Val Val Phe Val
            115                 120                 125 tcc aaa aag ggg ttg caa aaa att ttg aac gtg caa aaa aaa tta cca    432
Ser Lys Lys Gly Leu Gln Lys Ile Leu Asn Val Gln Lys Lys Leu Pro
        130                 135                 140 ata atc cag aaa att att atc atg gat tct aaa acg gat tac cag gga    480
Ile Ile Gln Lys Ile Ile Ile Met Asp Ser Lys Thr Asp Tyr Gln Gly
145                 150                 155                 160 ttt cag tcg atg tac acg ttc gtc aca tct cat cta cct ccc ggt ttt    528
Phe Gln Ser Met Tyr Thr Phe Val Thr Ser His Leu Pro Pro Gly Phe
                    165                 170                 175 aat gaa tac gat ttt gta cca gag tcc ttt gat cgt gac aaa aca att    576
Asn Glu Tyr Asp Phe Val Pro Glu Ser Phe Asp Arg Asp Lys Thr Ile
                180                 185                 190 gca ctg ata atg aat tcc tct gga tct act ggg tta cct aag ggt gtg    624
Ala Leu Ile Met Asn Ser Ser Gly Ser Thr Gly Leu Pro Lys Gly Val
            195                 200                 205 gcc ctt ccg cat aga act gcc tgc gtc aga ttc tcg cat gcc agg gat    672
Ala Leu Pro His Arg Thr Ala Cys Val Arg Phe Ser His Ala Arg Asp
        210                 215                 220 cct att ttt ggc aat caa atc att ccg gat act gcg att tta agt gtt    720
Pro Ile Phe Gly Asn Gln Ile Ile Pro Asp Thr Ala Ile Leu Ser Val
225                 230                 235                 240 gtt cca ttc cat cac ggt ttt gga atg ttt act aca ctc gga tat ttg    768
Val Pro Phe His His Gly Phe Gly Met Phe Thr Thr Leu Gly Tyr Leu
                    245                 250                 255 ata tgt gga ttt cga gtc gtc tta atg tat aga ttt gaa gaa gag ctg    816
Ile Cys Gly Phe Arg Val Val Leu Met Tyr Arg Phe Glu Glu Glu Leu
                260                 265                 270 ttt tta cga tcc ctt cag gat tac aaa att caa agt gcg ttg cta gta    864
Phe Leu Arg Ser Leu Gln Asp Tyr Lys Ile Gln Ser Ala Leu Leu Val
            275                 280                 285 cca acc cta ttt tca ttc ttc gcc aaa agc act ctg att gac aaa tac    912
Pro Thr Leu Phe Ser Phe Phe Ala Lys Ser Thr Leu Ile Asp Lys Tyr
        290                 295                 300 gat tta tct aat tta cac gaa att gct tct ggg ggc gca cct ctt tcg    960
Asp Leu Ser Asn Leu His Glu Ile Ala Ser Gly Gly Ala Pro Leu Ser
305                 310                 315                 320 aaa gaa gtc ggg gaa gcg gtt gca aaa cgg ttc cat ctt cca ggg ata   1008
Lys Glu Val Gly Glu Ala Val Ala Lys Arg Phe His Leu Pro Gly Ile
                    325                 330                 335 cga caa gga tat ggg ctc act gag act aca tca gct att ctg att aca   1056
Arg Gln Gly Tyr Gly Leu Thr Glu Thr Thr Ser Ala Ile Leu Ile Thr
                340                 345                 350 ccc gag ggg gat gat aaa ccg ggc gcg gtc ggt aaa gtt gtt cca ttt   1104
Pro Glu Gly Asp Asp Lys Pro Gly Ala Val Gly Lys Val Val Pro Phe
            355                 360                 365 ttt gaa gcg aag gtt gtg gat ctg gat acc ggg aaa acg ctg ggc gtt   1152
Phe Glu Ala Lys Val Val Asp Leu Asp Thr Gly Lys Thr Leu Gly Val
```

```
Phe Glu Ala Lys Val Val Asp Leu Asp Thr Gly Lys Thr Leu Gly Val
        370                 375                 380 aat cag aga ggc gaa tta tgt gtc aga gga cct atg att atg tcc ggt      1200
Asn Gln Arg Gly Glu Leu Cys Val Arg Gly Pro Met Ile Met Ser Gly
385                 390                 395                 400 tat gta aac aat ccg gaa gcg acc aac gcc ttg att gac aag gat gga      1248
Tyr Val Asn Asn Pro Glu Ala Thr Asn Ala Leu Ile Asp Lys Asp Gly
                405                 410                 415 tgg cta cat tct gga gac ata gct tac tgg gac gaa gac gaa cac ttc      1296
Trp Leu His Ser Gly Asp Ile Ala Tyr Trp Asp Glu Asp Glu His Phe
            420                 425                 430 ttc ata gtt gac cgc ttg aag tct tta att aaa tac aaa gga tat cag      1344
Phe Ile Val Asp Arg Leu Lys Ser Leu Ile Lys Tyr Lys Gly Tyr Gln
        435                 440                 445 gtg gcc ccc gct gaa ttg gaa tcg ata ttg tta caa cac ccc aac atc      1392
Val Ala Pro Ala Glu Leu Glu Ser Ile Leu Leu Gln His Pro Asn Ile
    450                 455                 460 ttc gac gcg ggc gtg gca ggt ctt ccc gac gat gac gcc ggt gaa ctt      1440
Phe Asp Ala Gly Val Ala Gly Leu Pro Asp Asp Asp Ala Gly Glu Leu
465                 470                 475                 480 ccc gcc gcc gtt gtt gtt ttg gag cac gga aag acg atg acg gaa aaa      1488
Pro Ala Ala Val Val Val Leu Glu His Gly Lys Thr Met Thr Glu Lys
                485                 490                 495 gag atc gtg gat tac gtc gcc agt caa gta aca acc gcg aaa aag ttg      1536
Glu Ile Val Asp Tyr Val Ala Ser Gln Val Thr Thr Ala Lys Lys Leu
            500                 505                 510 cgc gga gga gtt gtg ttt gtg gac gaa gta ccg aaa ggt ctt acc gga      1584
Arg Gly Gly Val Val Phe Val Asp Glu Val Pro Lys Gly Leu Thr Gly
        515                 520                 525 aaa ctc gac gca aga aaa atc aga gag atc ctc ata aag gcc aag aag      1632
Lys Leu Asp Ala Arg Lys Ile Arg Glu Ile Leu Ile Lys Ala Lys Lys
    530                 535                 540 ggc gga aag tcc aaa ttg taa                                         1653
Gly Gly Lys Ser Lys Leu
545                 550

<210> SEQ ID NO 12
<211> LENGTH: 1653
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(1650)
<223> OTHER INFORMATION: Photinus pyralis humanized type

<400> SEQUENCE: 12 atg gaa gat gcc aaa aac att aag aag ggc cca gcg cca ttc tac cca        48
Met Glu Asp Ala Lys Asn Ile Lys Lys Gly Pro Ala Pro Phe Tyr Pro
1               5                   10                  15 ctc gaa gac ggg acc gcc ggc gag cag ctg cac aaa gcc atg aag cgc        96
Leu Glu Asp Gly Thr Ala Gly Glu Gln Leu His Lys Ala Met Lys Arg
            20                  25                  30 tac gcc ctg gtg ccc ggc acc atc gcc ttt acc gac gca cat atc gag       144
Tyr Ala Leu Val Pro Gly Thr Ile Ala Phe Thr Asp Ala His Ile Glu
        35                  40                  45 gtg gac att acc tac gcc gag tac ttc gag atg agc gtt cgg ctg gca       192
Val Asp Ile Thr Tyr Ala Glu Tyr Phe Glu Met Ser Val Arg Leu Ala
    50                  55                  60 gaa gct atg aag cgc tat ggg ctg aat aca aac cat cgg atc gtg gtg       240
Glu Ala Met Lys Arg Tyr Gly Leu Asn Thr Asn His Arg Ile Val Val
```

```
                65                  70                  75                  80
tgc agc gag aat agc ttg cag ttc ttc atg ccc gtg ttg ggt gcc ctg        288
Cys Ser Glu Asn Ser Leu Gln Phe Phe Met Pro Val Leu Gly Ala Leu
                    85                  90                  95 ttc atc ggt gtg gct gtg gcc cca gct aac gac atc tac aac gag cgc        336
Phe Ile Gly Val Ala Val Ala Pro Ala Asn Asp Ile Tyr Asn Glu Arg
                    100                 105                 110 gag ctg ctg aac agc atg ggc atc agc cag ccc acc gtc gta ttc gtg        384
Glu Leu Leu Asn Ser Met Gly Ile Ser Gln Pro Thr Val Val Phe Val
                    115                 120                 125 agc aag aaa ggg ctg caa aag atc ctc aac gtg caa aag aag cta ccg        432
Ser Lys Lys Gly Leu Gln Lys Ile Leu Asn Val Gln Lys Lys Leu Pro
            130                 135                 140 atc ata caa aag atc atc atc atg gat agc aag acc gac tac cag ggc        480
Ile Ile Gln Lys Ile Ile Ile Met Asp Ser Lys Thr Asp Tyr Gln Gly
145                 150                 155                 160 ttc caa agc atg tac acc ttc gtg act tcc cat ttg cca ccc ggc ttc        528
Phe Gln Ser Met Tyr Thr Phe Val Thr Ser His Leu Pro Pro Gly Phe
                    165                 170                 175 aac gag tac gac ttc gtg ccc gag agc ttc gac cgg gac aaa acc atc        576
Asn Glu Tyr Asp Phe Val Pro Glu Ser Phe Asp Arg Asp Lys Thr Ile
                    180                 185                 190 gcc ctg atc atg aac agt agt ggc agt acc gga ttg ccc aag ggc gta        624
Ala Leu Ile Met Asn Ser Ser Gly Ser Thr Gly Leu Pro Lys Gly Val
                    195                 200                 205 gcc cta ccg cac cgc acc gct tgt gtc cga ttc agt cat gcc cgc gac        672
Ala Leu Pro His Arg Thr Ala Cys Val Arg Phe Ser His Ala Arg Asp
            210                 215                 220 ccc atc ttc ggc aac cag atc atc ccc gac acc gct atc ctc agc gtg        720
Pro Ile Phe Gly Asn Gln Ile Ile Pro Asp Thr Ala Ile Leu Ser Val
225                 230                 235                 240 gtg cca ttt cac cac ggc ttc ggc atg ttc acc acg ctg ggc tac ttg        768
Val Pro Phe His His Gly Phe Gly Met Phe Thr Thr Leu Gly Tyr Leu
                    245                 250                 255 atc tgc ggc ttt cgg gtc gtg ctc atg tac cgc ttc gag gag gag cta        816
Ile Cys Gly Phe Arg Val Val Leu Met Tyr Arg Phe Glu Glu Glu Leu
                    260                 265                 270 ttc ttg cgc agc ttg caa gac tat aag att caa tct gcc ctg ctg gtg        864
Phe Leu Arg Ser Leu Gln Asp Tyr Lys Ile Gln Ser Ala Leu Leu Val
                    275                 280                 285 ccc aca cta ttt agc ttc ttc gct aag agc act ctc atc gac aag tac        912
Pro Thr Leu Phe Ser Phe Phe Ala Lys Ser Thr Leu Ile Asp Lys Tyr
            290                 295                 300 gac cta agc aac ttg cac gag atc gcc agc ggc ggg gcg ccg ctc agc        960
Asp Leu Ser Asn Leu His Glu Ile Ala Ser Gly Gly Ala Pro Leu Ser
305                 310                 315                 320 aag gag gta ggt gag gcc gtg gcc aaa cgc ttc cac cta cca ggc atc        1008
Lys Glu Val Gly Glu Ala Val Ala Lys Arg Phe His Leu Pro Gly Ile
                    325                 330                 335 cgc cag ggc tac ggc ctg aca gaa aca acc agc gcc att ctg atc acc        1056
Arg Gln Gly Tyr Gly Leu Thr Glu Thr Thr Ser Ala Ile Leu Ile Thr
                    340                 345                 350 ccc gaa ggg gac gac aag cct ggc gca gta ggc aag gtg gtg ccc ttc        1104
Pro Glu Gly Asp Asp Lys Pro Gly Ala Val Gly Lys Val Val Pro Phe
                    355                 360                 365 ttc gag gct aag gtg gtg gac ttg gac acc ggt aag aca ctg ggt gtg        1152
Phe Glu Ala Lys Val Val Asp Leu Asp Thr Gly Lys Thr Leu Gly Val
                    370                 375                 380 aac cag cgc ggc gag ctg tgc gtc cgt ggc ccc atg atc atg agc ggc        1200
Asn Gln Arg Gly Glu Leu Cys Val Arg Gly Pro Met Ile Met Ser Gly
```

```
Asn Gln Arg Gly Glu Leu Cys Val Arg Gly Pro Met Ile Met Ser Gly
385                 390                 395                 400 tac gtt aac aac ccc gag gct aca aac gct ctc atc gac aag gac ggc      1248
Tyr Val Asn Asn Pro Glu Ala Thr Asn Ala Leu Ile Asp Lys Asp Gly
                    405                 410                 415 tgg ctg cac agc ggc gac atc gcc tac tgg gac gag gac gag cac ttc      1296
Trp Leu His Ser Gly Asp Ile Ala Tyr Trp Asp Glu Asp Glu His Phe
                420                 425                 430 ttc atc gtg gac cgg ctg aag agc ctg atc aaa tac aag ggc tac cag      1344
Phe Ile Val Asp Arg Leu Lys Ser Leu Ile Lys Tyr Lys Gly Tyr Gln
            435                 440                 445 gta gcc cca gcc gaa ctg gag agc atc ctg ctg caa cac ccc aac atc      1392
Val Ala Pro Ala Glu Leu Glu Ser Ile Leu Leu Gln His Pro Asn Ile
450                 455                 460 ttc gac gcc ggg gtc gcc ggc ctg ccc gac gac gat gcc ggc gag ctg      1440
Phe Asp Ala Gly Val Ala Gly Leu Pro Asp Asp Asp Ala Gly Glu Leu
465                 470                 475                 480 ccc gcc gca gtc gtc gtg ctg gaa cac ggt aaa acc atg acc gag aag      1488
Pro Ala Ala Val Val Val Leu Glu His Gly Lys Thr Met Thr Glu Lys
                485                 490                 495 gag atc gtg gac tat gtg gcc agc cag gtt aca acc gcc aag aag ctg      1536
Glu Ile Val Asp Tyr Val Ala Ser Gln Val Thr Thr Ala Lys Lys Leu
                500                 505                 510 cgc ggt ggt gtt gtg ttc gtg gac gag gtg cct aaa gga ctg acc ggc      1584
Arg Gly Gly Val Val Phe Val Asp Glu Val Pro Lys Gly Leu Thr Gly
            515                 520                 525 aag ttg gac gcc cgc aag atc cgc gag att ctc att aag gcc aag aag      1632
Lys Leu Asp Ala Arg Lys Ile Arg Glu Ile Leu Ile Lys Ala Lys Lys
530                 535                 540 ggc ggc aag atc gcc gtg taa                                          1653
Gly Gly Lys Ile Ala Val
545                 550

<210> SEQ ID NO 13
<211> LENGTH: 1653
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(1650)
<223> OTHER INFORMATION: Photinus pyralis optimized type

<400> SEQUENCE: 13 atg gag gac gcc aag aac atc aag aag ggc ccc gcc ccc ttt tac ccc       48
Met Glu Asp Ala Lys Asn Ile Lys Lys Gly Pro Ala Pro Phe Tyr Pro
1               5                   10                  15 ctg gag gac ggc acc gcc ggc gag cag ctg cac aag gcc atg aag aga       96
Leu Glu Asp Gly Thr Ala Gly Glu Gln Leu His Lys Ala Met Lys Arg
                20                  25                  30 tac gcc ctg gtc ccc ggc acc atc gcc ttt acc gac gcc cac atc gag      144
Tyr Ala Leu Val Pro Gly Thr Ile Ala Phe Thr Asp Ala His Ile Glu
            35                  40                  45 gtc aac atc acc tac gcc gag tac ttt gag atg agc gtc aga ctg gcc      192
Val Asn Ile Thr Tyr Ala Glu Tyr Phe Glu Met Ser Val Arg Leu Ala
50                  55                  60 gag gcc atg aag aga tac ggc ctg aac acc aac cac aga atc gtc gtg      240
Glu Ala Met Lys Arg Tyr Gly Leu Asn Thr Asn His Arg Ile Val Val
65                  70                  75                  80 tgc agc gag aac agc ctc cag ttt ttt atg ccc gtc ctg ggc gcc ctg      288
Cys Ser Glu Asn Ser Leu Gln Phe Phe Met Pro Val Leu Gly Ala Leu
```

```
                        85                  90                  95
ttt atc ggc gtc gcc gtc gcc ccc gcc aac gac atc tac aac gag aga      336
Phe Ile Gly Val Ala Val Ala Pro Ala Asn Asp Ile Tyr Asn Glu Arg
            100                 105                 110 gag ctg ctg aac agc atg aac atc agc cag ccc acc gtc gtc ttt gtc      384
Glu Leu Leu Asn Ser Met Asn Ile Ser Gln Pro Thr Val Val Phe Val
            115                 120                 125 agc aag aag ggc ctc cag aag atc ctg aac gtc cag aag aag ctg ccc      432
Ser Lys Lys Gly Leu Gln Lys Ile Leu Asn Val Gln Lys Lys Leu Pro
        130                 135                 140 atc atc cag aag atc atc atc atg gac agc aag acc gac tac cag ggc      480
Ile Ile Gln Lys Ile Ile Ile Met Asp Ser Lys Thr Asp Tyr Gln Gly
145                 150                 155                 160 ttt cag agc atg tac acc ttt gtc acc agc cac ctg ccc ccc ggc ttt      528
Phe Gln Ser Met Tyr Thr Phe Val Thr Ser His Leu Pro Pro Gly Phe
                165                 170                 175 aac gag tac gac ttt gtc ccc gag agc ttt gac aga gac aag acc atc      576
Asn Glu Tyr Asp Phe Val Pro Glu Ser Phe Asp Arg Asp Lys Thr Ile
            180                 185                 190 gcc ctg atc atg aac agc agc ggc agc acc ggc ctg ccc aag ggc gtc      624
Ala Leu Ile Met Asn Ser Ser Gly Ser Thr Gly Leu Pro Lys Gly Val
            195                 200                 205 gcc ctg ccc cac aga acc gcc tgc gtc aga ttt agc cac gcc aga gac      672
Ala Leu Pro His Arg Thr Ala Cys Val Arg Phe Ser His Ala Arg Asp
        210                 215                 220 ccc atc ttt ggc aac cag atc atc ccc gac acc gcc atc ctg agc gtc      720
Pro Ile Phe Gly Asn Gln Ile Ile Pro Asp Thr Ala Ile Leu Ser Val
225                 230                 235                 240 gtc ccc ttt cac cac ggc ttt ggc atg ttt acc acc ctg ggc tac ctg      768
Val Pro Phe His His Gly Phe Gly Met Phe Thr Thr Leu Gly Tyr Leu
                245                 250                 255 atc tgc ggc ttt aga gtc gtc ctg atg tac aga ttt gag gag gag ctg      816
Ile Cys Gly Phe Arg Val Val Leu Met Tyr Arg Phe Glu Glu Glu Leu
            260                 265                 270 ttt ctg aga agc ctg cag gac tac aag atc cag agc gcc ctg ctg gtc      864
Phe Leu Arg Ser Leu Gln Asp Tyr Lys Ile Gln Ser Ala Leu Leu Val
        275                 280                 285 ccc acc ctg ttt agc ttt ttt gcc aag agc acc ctg atc gac aag tac      912
Pro Thr Leu Phe Ser Phe Phe Ala Lys Ser Thr Leu Ile Asp Lys Tyr
290                 295                 300 gac ctg agc aac ctg cac gag atc gcc agc ggc ggc gcc ccc ctg agc      960
Asp Leu Ser Asn Leu His Glu Ile Ala Ser Gly Gly Ala Pro Leu Ser
305                 310                 315                 320 aag gag gtc ggc gag gcc gtc gcc aag aga ttt cac ctg ccc ggc atc     1008
Lys Glu Val Gly Glu Ala Val Ala Lys Arg Phe His Leu Pro Gly Ile
                325                 330                 335 aga cag ggc tac ggc ctg acc gag acc acc agc gcc atc ctg atc acc     1056
Arg Gln Gly Tyr Gly Leu Thr Glu Thr Thr Ser Ala Ile Leu Ile Thr
            340                 345                 350 ccc gag ggc gac gac aag ccc ggc gcc gtc ggc aag gtc gtc ccc ttt     1104
Pro Glu Gly Asp Asp Lys Pro Gly Ala Val Gly Lys Val Val Pro Phe
        355                 360                 365 ttt gag gcc aag gtc gtg gac ctg gac acc ggc aag acc ctg ggc gtc     1152
Phe Glu Ala Lys Val Val Asp Leu Asp Thr Gly Lys Thr Leu Gly Val
370                 375                 380 aac cag aga ggc gag ctg tgc gtc aga ggc ccc atg atc atg agc ggc     1200
Asn Gln Arg Gly Glu Leu Cys Val Arg Gly Pro Met Ile Met Ser Gly
385                 390                 395                 400 tac gtc aac aac ccc gag gcc acc aac gcc ctg atc gac aag gac ggc     1248
```

```
                Tyr Val Asn Asn Pro Glu Ala Thr Asn Ala Leu Ile Asp Lys Asp Gly
                                405                 410                 415 tgg ctg cac agc ggc gac atc gcc tac tgg gac gag gac gag cac ttt       1296
Trp Leu His Ser Gly Asp Ile Ala Tyr Trp Asp Glu Asp Glu His Phe
            420                 425                 430 ttt atc gtg gac aga ctg aag agc ctg atc aag tac aag ggc tac cag       1344
Phe Ile Val Asp Arg Leu Lys Ser Leu Ile Lys Tyr Lys Gly Tyr Gln
                435                 440                 445 gtc gcc ccc gcc gag ctg gag agc atc ctg ctc cag cac ccc aac atc       1392
Val Ala Pro Ala Glu Leu Glu Ser Ile Leu Leu Gln His Pro Asn Ile
    450                 455                 460 ttt gac gcc ggc gtc gcc ggc ctg ccc gac gac gac gcc ggc gag ctg       1440
Phe Asp Ala Gly Val Ala Gly Leu Pro Asp Asp Asp Ala Gly Glu Leu
465                 470                 475                 480 ccc gcc gcc gtc gtc gtc ctg gag cac ggc aag acc atg acc gag aag       1488
Pro Ala Ala Val Val Val Leu Glu His Gly Lys Thr Met Thr Glu Lys
                485                 490                 495 gag atc gtg gac tac gtc gcc agc cag gtc acc acc gcc aag aag ctg       1536
Glu Ile Val Asp Tyr Val Ala Ser Gln Val Thr Thr Ala Lys Lys Leu
                500                 505                 510 aga ggc ggc gtc gtc ttt gtg gac gag gtc ccc aag ggc ctg acc ggc       1584
Arg Gly Gly Val Val Phe Val Asp Glu Val Pro Lys Gly Leu Thr Gly
            515                 520                 525 aag ctg gac gcc aga aag atc aga gag atc ctg atc aag gcc aag aag       1632
Lys Leu Asp Ala Arg Lys Ile Arg Glu Ile Leu Ile Lys Ala Lys Lys
530                 535                 540 ggc ggc aag agc aag ctg taa                                           1653
Gly Gly Lys Ser Lys Leu
545                 550

<210> SEQ ID NO 14
<211> LENGTH: 1647
<212> TYPE: DNA
<213> ORGANISM: Luciola cruciata
<220> FEATURE:
<221> NAME/KEY: CDS
<222> LOCATION: (1)..(1644)

<400> SEQUENCE: 14 atg gaa aac atg gaa aac gat gaa aat att gta gtt gga cct aaa ccg        48
Met Glu Asn Met Glu Asn Asp Glu Asn Ile Val Val Gly Pro Lys Pro
1               5                   10                  15 ttt tac cct atc gaa gag gga tct gct gga aca caa tta cgc aaa tac        96
Phe Tyr Pro Ile Glu Glu Gly Ser Ala Gly Thr Gln Leu Arg Lys Tyr
                20                  25                  30 atg gag cga tat gca aaa ctt ggc gca att gct ttt aca aat gca gtt       144
Met Glu Arg Tyr Ala Lys Leu Gly Ala Ile Ala Phe Thr Asn Ala Val
            35                  40                  45 act ggt gtt gat tat tct tac gcc gaa tac ttg gag aaa tca tgt tgt       192
Thr Gly Val Asp Tyr Ser Tyr Ala Glu Tyr Leu Glu Lys Ser Cys Cys
        50                  55                  60 cta gga aaa gct ttg caa aat tat ggt ttg gtt gtt gat ggc aga att       240
Leu Gly Lys Ala Leu Gln Asn Tyr Gly Leu Val Val Asp Gly Arg Ile
65                  70                  75                  80 gcg tta tgc agt gaa aac tgt gaa gaa ttt ttt att cct gta ata gcc       288
Ala Leu Cys Ser Glu Asn Cys Glu Glu Phe Phe Ile Pro Val Ile Ala
                85                  90                  95 gga ctg ttt ata ggt gta ggt gtt gca ccc act aat gag att tac act       336
Gly Leu Phe Ile Gly Val Gly Val Ala Pro Thr Asn Glu Ile Tyr Thr
                100                 105                 110 tta cgt gaa ctg gtt cac agt tta ggt atc tct aaa cca aca att gta       384
```

```
Leu Arg Glu Leu Val His Ser Leu Gly Ile Ser Lys Pro Thr Ile Val
        115                 120                 125 ttt agt tct aaa aaa ggc tta gat aaa gtt ata aca gta cag aaa aca       432
Phe Ser Ser Lys Lys Gly Leu Asp Lys Val Ile Thr Val Gln Lys Thr
130                 135                 140 gta act act att aaa acc att gtt ata cta gat agc aaa gtt gat tat       480
Val Thr Thr Ile Lys Thr Ile Val Ile Leu Asp Ser Lys Val Asp Tyr
145                 150                 155                 160 cga gga tat caa tgt ctg gac acc ttt ata aaa aga aac act cca cca       528
Arg Gly Tyr Gln Cys Leu Asp Thr Phe Ile Lys Arg Asn Thr Pro Pro
                165                 170                 175 ggt ttt caa gca tcc agt ttc aaa act gtg gaa gtt gac cgt aaa gaa       576
Gly Phe Gln Ala Ser Ser Phe Lys Thr Val Glu Val Asp Arg Lys Glu
            180                 185                 190 caa gtt gct ctt ata atg aac tct tcg ggt tct acc ggt ttg cca aaa       624
Gln Val Ala Leu Ile Met Asn Ser Ser Gly Ser Thr Gly Leu Pro Lys
        195                 200                 205 ggc gta caa ctt act cac gaa aat aca gtc act aga ttt tct cat gct       672
Gly Val Gln Leu Thr His Glu Asn Thr Val Thr Arg Phe Ser His Ala
210                 215                 220 aga gat ccg att tat ggt aac caa gtt tca cca ggc acc gct gtt tta       720
Arg Asp Pro Ile Tyr Gly Asn Gln Val Ser Pro Gly Thr Ala Val Leu
225                 230                 235                 240 act gtc gtt cca ttc cat cat ggt ttt ggt atg ttc act act cta ggg       768
Thr Val Val Pro Phe His His Gly Phe Gly Met Phe Thr Thr Leu Gly
                245                 250                 255 tat tta att tgt ggt ttt cgt gtt gta atg tta aca aaa ttc gat gaa       816
Tyr Leu Ile Cys Gly Phe Arg Val Val Met Leu Thr Lys Phe Asp Glu
            260                 265                 270 gaa aca ttt tta aaa act cta caa gat tat aaa tgt aca agt gtt att       864
Glu Thr Phe Leu Lys Thr Leu Gln Asp Tyr Lys Cys Thr Ser Val Ile
        275                 280                 285 ctt gta ccg acc ttg ttt gca att ctc aac aaa agt gaa tta ctc aat       912
Leu Val Pro Thr Leu Phe Ala Ile Leu Asn Lys Ser Glu Leu Leu Asn
290                 295                 300 aaa tac gat ttg tca aat tta gtt gag att gca tct ggc gga gca cct       960
Lys Tyr Asp Leu Ser Asn Leu Val Glu Ile Ala Ser Gly Gly Ala Pro
305                 310                 315                 320 tta tca aaa gaa gtt ggt gaa gct gtt gct aga cgc ttt aat ctt ccc      1008
Leu Ser Lys Glu Val Gly Glu Ala Val Ala Arg Arg Phe Asn Leu Pro
                325                 330                 335 ggt gtt cgt caa ggt tat ggt tta aca gaa aca aca tct gcc att att      1056
Gly Val Arg Gln Gly Tyr Gly Leu Thr Glu Thr Thr Ser Ala Ile Ile
            340                 345                 350 att aca cca gaa gga gac gat aaa cca gga gct tct gga aaa gtc gtg      1104
Ile Thr Pro Glu Gly Asp Asp Lys Pro Gly Ala Ser Gly Lys Val Val
        355                 360                 365 ccg ttg ttt aaa gca aaa gtt att gat ctt gat acc aaa aaa tct tta      1152
Pro Leu Phe Lys Ala Lys Val Ile Asp Leu Asp Thr Lys Lys Ser Leu
370                 375                 380 ggt cct aac aga cgt gga gaa gtt tgt gtt aaa gga cct atg ctt atg      1200
Gly Pro Asn Arg Arg Gly Glu Val Cys Val Lys Gly Pro Met Leu Met
385                 390                 395                 400 aaa ggt tat gta aat aat cca gaa gca aca aaa gaa ctt att gac gaa      1248
Lys Gly Tyr Val Asn Asn Pro Glu Ala Thr Lys Glu Leu Ile Asp Glu
                405                 410                 415 gaa ggt tgg ctg cac acc gga gat att gga tat tat gat gaa gaa aaa      1296
Glu Gly Trp Leu His Thr Gly Asp Ile Gly Tyr Tyr Asp Glu Glu Lys
            420                 425                 430
```

```
cat ttc ttt att gtc gat cgt ttg aag tct tta atc aaa tac aaa gga     1344
His Phe Phe Ile Val Asp Arg Leu Lys Ser Leu Ile Lys Tyr Lys Gly
        435                 440                 445 tac caa gta cca cct gcc gaa tta gaa tcc gtt ctt ttg caa cat cca     1392
Tyr Gln Val Pro Pro Ala Glu Leu Glu Ser Val Leu Leu Gln His Pro
450                 455                 460 tct atc ttt gat gct ggt gtt gcc ggc gtt cct gat cct gta gct ggc     1440
Ser Ile Phe Asp Ala Gly Val Ala Gly Val Pro Asp Pro Val Ala Gly
465                 470                 475                 480 gag ctt cca gga gcc gtt gtt gta ctg gaa agc gga aaa aat atg acc     1488
Glu Leu Pro Gly Ala Val Val Val Leu Glu Ser Gly Lys Asn Met Thr
                485                 490                 495 gaa aaa gaa gta atg gat tat gtt gca agt caa gtt tca aat gca aaa     1536
Glu Lys Glu Val Met Asp Tyr Val Ala Ser Gln Val Ser Asn Ala Lys
            500                 505                 510 cgt tta cgt ggt ggt gtt cgt ttt gtg gat gaa gta cct aaa ggt ctt     1584
Arg Leu Arg Gly Gly Val Arg Phe Val Asp Glu Val Pro Lys Gly Leu
        515                 520                 525 act gga aaa att gac ggc aga gca att aga gaa atc ctt aag aaa cca     1632
Thr Gly Lys Ile Asp Gly Arg Ala Ile Arg Glu Ile Leu Lys Lys Pro
    530                 535                 540 gtt gct aag atg tga                                                 1647
Val Ala Lys Met
545

<210> SEQ ID NO 15
<211> LENGTH: 1647
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(1644)
<223> OTHER INFORMATION: Luciola cruciata humanized type

<400> SEQUENCE: 15 atg gag aac atg gag aat gac gaa aac atc gtg gtg ggc ccc aaa ccc       48
Met Glu Asn Met Glu Asn Asp Glu Asn Ile Val Val Gly Pro Lys Pro
1               5                  10                  15 ttt tat ccc att gaa gag ggg tcc gca ggg aca cag tta cgt aag tac       96
Phe Tyr Pro Ile Glu Glu Gly Ser Ala Gly Thr Gln Leu Arg Lys Tyr
            20                  25                  30 atg gaa cgt tac gcc aaa ctt gga gcc att gcc ttt act aac gct gtt      144
Met Glu Arg Tyr Ala Lys Leu Gly Ala Ile Ala Phe Thr Asn Ala Val
        35                  40                  45 act ggg gtc gat tac agc tac gct gag tat ctg gag aaa agc tgc tgt      192
Thr Gly Val Asp Tyr Ser Tyr Ala Glu Tyr Leu Glu Lys Ser Cys Cys
50                  55                  60 ctg gga aag gcc cta cag aat tat ggg ttg gtt gtg gac gga cgc att      240
Leu Gly Lys Ala Leu Gln Asn Tyr Gly Leu Val Val Asp Gly Arg Ile
65                  70                  75                  80 gcc ctt tgc tca gag aac tgt gag gag ttc ttt att ccg gta ata gcg      288
Ala Leu Cys Ser Glu Asn Cys Glu Glu Phe Phe Ile Pro Val Ile Ala
                85                  90                  95 gga ctt ttt att ggc gtg ggt gtt gca cct acg aac gaa ata tac acc      336
Gly Leu Phe Ile Gly Val Gly Val Ala Pro Thr Asn Glu Ile Tyr Thr
            100                 105                 110 ctt cgg gag ctc gtg cat tca ctg ggt atc tcc aag cca aca att gtg      384
Leu Arg Glu Leu Val His Ser Leu Gly Ile Ser Lys Pro Thr Ile Val
        115                 120                 125 ttt tcc tcg aaa aag ggg ctc gac aaa gtt att acc gtg cag aag aca      432
```

```
Phe Ser Ser Lys Lys Gly Leu Asp Lys Val Ile Thr Val Gln Lys Thr
        130             135                 140 gtc aca acg atc aag act atc gtc atc ctg gac tcc aaa gtg gac tat      480
Val Thr Thr Ile Lys Thr Ile Val Ile Leu Asp Ser Lys Val Asp Tyr
145                 150                 155                 160 cgc ggg tat cag tgt ctg gat acc ttc atc aaa cgc aat act cct ccc      528
Arg Gly Tyr Gln Cys Leu Asp Thr Phe Ile Lys Arg Asn Thr Pro Pro
                165                 170                 175 ggt ttt cag gcc tcc tcc ttc aag aca gtc gag gta gat cgc aag gag      576
Gly Phe Gln Ala Ser Ser Phe Lys Thr Val Glu Val Asp Arg Lys Glu
            180                 185                 190 cag gtg gct cta atc atg aat agc agt ggc tct act ggg tta ccc aaa      624
Gln Val Ala Leu Ile Met Asn Ser Ser Gly Ser Thr Gly Leu Pro Lys
        195                 200                 205 ggc gtt caa ctg acc cac gag aat acg gtg acc aga ttc tct cac gct      672
Gly Val Gln Leu Thr His Glu Asn Thr Val Thr Arg Phe Ser His Ala
    210                 215                 220 aga gat ccc ata tac ggc aat cag gtg tct cct ggt aca gca gtg ctg      720
Arg Asp Pro Ile Tyr Gly Asn Gln Val Ser Pro Gly Thr Ala Val Leu
225                 230                 235                 240 act gtt gtg cca ttt cat cac ggc ttt ggc atg ttt aca acc ctc ggt      768
Thr Val Val Pro Phe His His Gly Phe Gly Met Phe Thr Thr Leu Gly
                245                 250                 255 tac ctc att tgt ggg ttc aga gtg gtg atg ttg aca aag ttt gat gag      816
Tyr Leu Ile Cys Gly Phe Arg Val Val Met Leu Thr Lys Phe Asp Glu
            260                 265                 270 gag act ttc ctg aaa acc ttg cag gac tac aaa tgc acc agt gtc att      864
Glu Thr Phe Leu Lys Thr Leu Gln Asp Tyr Lys Cys Thr Ser Val Ile
        275                 280                 285 ctt gtg ccc act ctg ttc gcc ata ctc aac aaa tca gag ctg ctc aac      912
Leu Val Pro Thr Leu Phe Ala Ile Leu Asn Lys Ser Glu Leu Leu Asn
    290                 295                 300 aag tat gac ctc agc aat ctg gtg gag att gcc tct ggt gga gcc cct      960
Lys Tyr Asp Leu Ser Asn Leu Val Glu Ile Ala Ser Gly Gly Ala Pro
305                 310                 315                 320 ctg agt aag gaa gtc gga gaa gct gtc gct cgg aga ttc aac ttg cct     1008
Leu Ser Lys Glu Val Gly Glu Ala Val Ala Arg Arg Phe Asn Leu Pro
                325                 330                 335 ggc gtt cgg caa ggc tac ggg cta act gag acc acg tct gca atc atc     1056
Gly Val Arg Gln Gly Tyr Gly Leu Thr Glu Thr Thr Ser Ala Ile Ile
            340                 345                 350 att acc cca gag gga gat gat aaa ccg ggt gca tca ggg aag gta gtg     1104
Ile Thr Pro Glu Gly Asp Asp Lys Pro Gly Ala Ser Gly Lys Val Val
        355                 360                 365 ccc ctg ttt aaa gct aag gtc ata gat ctg gac aca aag aag tct tta     1152
Pro Leu Phe Lys Ala Lys Val Ile Asp Leu Asp Thr Lys Lys Ser Leu
    370                 375                 380 ggc cct aat agg cga ggt gag gtc tgc gtg aag gga cca atg ctg atg     1200
Gly Pro Asn Arg Arg Gly Glu Val Cys Val Lys Gly Pro Met Leu Met
385                 390                 395                 400 aag ggc tac gta aac aat ccc gaa gcg aca aag gaa ctg atc gac gaa     1248
Lys Gly Tyr Val Asn Asn Pro Glu Ala Thr Lys Glu Leu Ile Asp Glu
                405                 410                 415 gaa gga tgg tta cat acc ggc gac ata ggg tac tat gac gag gag aag     1296
Glu Gly Trp Leu His Thr Gly Asp Ile Gly Tyr Tyr Asp Glu Glu Lys
            420                 425                 430 cac ttc ttc att gtg gat agg ctg aaa tcg cta atc aag tat aag ggg     1344
His Phe Phe Ile Val Asp Arg Leu Lys Ser Leu Ile Lys Tyr Lys Gly
        435                 440                 445
```

```
tat caa gtg cca cca gcc gaa ctg gaa agt gtg ctg ctc cag cac cca    1392
Tyr Gln Val Pro Pro Ala Glu Leu Glu Ser Val Leu Leu Gln His Pro
    450                 455                 460 agc atc ttc gat gct gga gtt gcc ggc gtg cct gat cca gtc gct ggg    1440
Ser Ile Phe Asp Ala Gly Val Ala Gly Val Pro Asp Pro Val Ala Gly
465                 470                 475                 480 gaa ctc cct gga gcc gtc gtc gta ctc gaa agc gga aag aac atg acc    1488
Glu Leu Pro Gly Ala Val Val Val Leu Glu Ser Gly Lys Asn Met Thr
                485                 490                 495 gaa aaa gag gtg atg gac tac gtt gca tcc cag gtg agc aac gcc aag    1536
Glu Lys Glu Val Met Asp Tyr Val Ala Ser Gln Val Ser Asn Ala Lys
            500                 505                 510 cgg ttg aga ggc gga gta cga ttc gtg gat gaa gtg ccc aaa ggc ctt    1584
Arg Leu Arg Gly Gly Val Arg Phe Val Asp Glu Val Pro Lys Gly Leu
        515                 520                 525 acc ggc aaa atc gac ggc aga gcg atc agg gag atc ttg aaa aag ccg    1632
Thr Gly Lys Ile Asp Gly Arg Ala Ile Arg Glu Ile Leu Lys Lys Pro
    530                 535                 540 gtt gca aaa atg taa                                                1647
Val Ala Lys Met
545

<210> SEQ ID NO 16
<211> LENGTH: 1647
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(1644)
<223> OTHER INFORMATION: Luciola cruciata optimized type

<400> SEQUENCE: 16 atg gag aac atg gag aac gac gag aac atc gtc gtc ggc ccc aag ccc    48
Met Glu Asn Met Glu Asn Asp Glu Asn Ile Val Val Gly Pro Lys Pro
1               5                  10                  15 ttt tac ccc atc gag gag ggc agc gcc ggc acc cag ctg agg aag tac    96
Phe Tyr Pro Ile Glu Glu Gly Ser Ala Gly Thr Gln Leu Arg Lys Tyr
                20                  25                  30 atg gag agg tac gcc aag ctg ggc gcc atc gcc ttt acc aac gcc gtc    144
Met Glu Arg Tyr Ala Lys Leu Gly Ala Ile Ala Phe Thr Asn Ala Val
            35                  40                  45 acc ggc gtg gac tac agc tac gcc gag tac ctg gag aag agc tgc tgc    192
Thr Gly Val Asp Tyr Ser Tyr Ala Glu Tyr Leu Glu Lys Ser Cys Cys
        50                  55                  60 ctg ggc aag gcc ctc cag aac tac ggc ctg gtc gtg gac ggc agg atc    240
Leu Gly Lys Ala Leu Gln Asn Tyr Gly Leu Val Val Asp Gly Arg Ile
65                  70                  75                  80 gcc ctg tgc agc gag aac tgc gag gag ttt ttt atc ccc gtc atc gcc    288
Ala Leu Cys Ser Glu Asn Cys Glu Glu Phe Phe Ile Pro Val Ile Ala
                85                  90                  95 ggc ctg ttt atc ggc gtc ggc gtc gcc ccc acc aac gag atc tac acc    336
Gly Leu Phe Ile Gly Val Gly Val Ala Pro Thr Asn Glu Ile Tyr Thr
                100                 105                 110 ctg agg gag ctg gtc cac agc ctg ggc atc agc aag ccc acc atc gtc    384
Leu Arg Glu Leu Val His Ser Leu Gly Ile Ser Lys Pro Thr Ile Val
            115                 120                 125 ttt agc agc aag aag ggc ctg gac aag gtc atc acc gtc cag aag acc    432
Phe Ser Ser Lys Lys Gly Leu Asp Lys Val Ile Thr Val Gln Lys Thr
        130                 135                 140 gtc acc acc atc aag acc atc gtc atc ctg gac agc aag gtg gac tac    480
```

```
Val Thr Thr Ile Lys Thr Ile Val Ile Leu Asp Ser Lys Val Asp Tyr
145                 150                 155                 160 agg ggc tac cag tgc ctg gac acc ttt atc aag agg aac acc ccc ccc       528
Arg Gly Tyr Gln Cys Leu Asp Thr Phe Ile Lys Arg Asn Thr Pro Pro
                165                 170                 175 ggc ttt cag gcc agc agc ttt aag acc gtc gag gtg gac agg aag gag       576
Gly Phe Gln Ala Ser Ser Phe Lys Thr Val Glu Val Asp Arg Lys Glu
            180                 185                 190 cag gtc gcc ctg atc atg aac agc agc ggc agc acc ggc ctg ccc aag       624
Gln Val Ala Leu Ile Met Asn Ser Ser Gly Ser Thr Gly Leu Pro Lys
        195                 200                 205 ggc gtc cag ctg acc cac gag aac acc gtc acc agg ttt agc cac gcc       672
Gly Val Gln Leu Thr His Glu Asn Thr Val Thr Arg Phe Ser His Ala
    210                 215                 220 agg gac ccc atc tac ggc aac cag gtc agc ccc ggc acc gcc gtc ctg       720
Arg Asp Pro Ile Tyr Gly Asn Gln Val Ser Pro Gly Thr Ala Val Leu
225                 230                 235                 240 acc gtc gtc ccc ttt cac cac ggc ttt ggc atg ttt acc acc ctg ggc       768
Thr Val Val Pro Phe His His Gly Phe Gly Met Phe Thr Thr Leu Gly
                245                 250                 255 tac ctg atc tgc ggc ttt agg gtc gtc atg ctg acc aag ttt gac gag       816
Tyr Leu Ile Cys Gly Phe Arg Val Val Met Leu Thr Lys Phe Asp Glu
            260                 265                 270 gag acc ttt ctg aag acc ctg cag gac tac aag tgc acc agc gtc atc       864
Glu Thr Phe Leu Lys Thr Leu Gln Asp Tyr Lys Cys Thr Ser Val Ile
        275                 280                 285 ctg gtc ccc acc ctg ttt gcc atc ctg aac aag agc gag ctg ctg aac       912
Leu Val Pro Thr Leu Phe Ala Ile Leu Asn Lys Ser Glu Leu Leu Asn
    290                 295                 300 aag tac gac ctg agc aac ctg gtc gag atc gcc agc ggc ggc gcc ccc       960
Lys Tyr Asp Leu Ser Asn Leu Val Glu Ile Ala Ser Gly Gly Ala Pro
305                 310                 315                 320 ctg agc aag gag gtc ggc gag gcc gtc gcc agg agg ttt aac ctg ccc      1008
Leu Ser Lys Glu Val Gly Glu Ala Val Ala Arg Arg Phe Asn Leu Pro
                325                 330                 335 ggc gtc agg cag ggc tac ggc ctg acc gag acc acc agc gcc atc atc      1056
Gly Val Arg Gln Gly Tyr Gly Leu Thr Glu Thr Thr Ser Ala Ile Ile
            340                 345                 350 atc acc ccc gag ggc gac gac aag ccc ggc gcc agc ggc aag gtc gtc      1104
Ile Thr Pro Glu Gly Asp Asp Lys Pro Gly Ala Ser Gly Lys Val Val
        355                 360                 365 ccc ctg ttt aag gcc aag gtc atc gac ctg gac acc aag aag agc ctg      1152
Pro Leu Phe Lys Ala Lys Val Ile Asp Leu Asp Thr Lys Lys Ser Leu
    370                 375                 380 ggc ccc aac agg agg ggc gag gtc tgc gtc aag ggc ccc atg ctg atg      1200
Gly Pro Asn Arg Arg Gly Glu Val Cys Val Lys Gly Pro Met Leu Met
385                 390                 395                 400 aag ggc tac gtc aac aac ccc gag gcc acc aag gag ctg atc gac gag      1248
Lys Gly Tyr Val Asn Asn Pro Glu Ala Thr Lys Glu Leu Ile Asp Glu
                405                 410                 415 gag ggc tgg ctg cac acc ggc gac atc ggc tac tac gac gag gag aag      1296
Glu Gly Trp Leu His Thr Gly Asp Ile Gly Tyr Tyr Asp Glu Glu Lys
            420                 425                 430 cac ttt ttt atc gtg gac agg ctg aag agc ctg atc aag tac aag ggc      1344
His Phe Phe Ile Val Asp Arg Leu Lys Ser Leu Ile Lys Tyr Lys Gly
        435                 440                 445 tac cag gtc ccc ccc gcc gag ctg gag agc gtc ctg ctc cag cac ccc      1392
Tyr Gln Val Pro Pro Ala Glu Leu Glu Ser Val Leu Leu Gln His Pro
    450                 455                 460
```

-continued

```
agc atc ttt gac gcc ggc gtc gcc ggc gtc ccc gac ccc gtc gcc ggc       1440
Ser Ile Phe Asp Ala Gly Val Ala Gly Val Pro Asp Pro Val Ala Gly
465             470                 475                 480 gag ctg ccc ggc gcc gtc gtc gtc ctg gag agc ggc aag aac atg acc       1488
Glu Leu Pro Gly Ala Val Val Val Leu Glu Ser Gly Lys Asn Met Thr
            485                 490                 495 gag aag gag gtc atg gac tac gtc gcc agc cag gtc agc aac gcc aag       1536
Glu Lys Glu Val Met Asp Tyr Val Ala Ser Gln Val Ser Asn Ala Lys
500                 505                 510 agg ctg agg ggc ggc gtc agg ttt gtg gac gag gtc ccc aag ggc ctg       1584
Arg Leu Arg Gly Gly Val Arg Phe Val Asp Glu Val Pro Lys Gly Leu
            515                 520                 525 acc ggc aag atc gac ggc agg gcc atc agg gag atc ctg aag aag ccc       1632
Thr Gly Lys Ile Asp Gly Arg Ala Ile Arg Glu Ile Leu Lys Lys Pro
530                 535                 540 gtc gcc aag atg tga                                                   1647
Val Ala Lys Met
545

<210> SEQ ID NO 17
<211> LENGTH: 936
<212> TYPE: DNA
<213> ORGANISM: Renilla reniformis
<220> FEATURE:
<221> NAME/KEY: CDS
<222> LOCATION: (1)..(933)

<400> SEQUENCE: 17 atg act tcg aaa gtt tat gat cca gaa caa agg aaa cgg atg ata act        48
Met Thr Ser Lys Val Tyr Asp Pro Glu Gln Arg Lys Arg Met Ile Thr
1               5                   10                  15 ggt ccg cag tgg tgg gcc aga tgt aaa caa atg aat gtt ctt gat tca        96
Gly Pro Gln Trp Trp Ala Arg Cys Lys Gln Met Asn Val Leu Asp Ser
            20                  25                  30 ttt att aat tat tat gat tca gaa aaa cat gca gaa aat gct gtt att       144
Phe Ile Asn Tyr Tyr Asp Ser Glu Lys His Ala Glu Asn Ala Val Ile
        35                  40                  45 ttt tta cat ggt aac gcg gcc tct tct tat tta tgg cga cat gtt gtg       192
Phe Leu His Gly Asn Ala Ala Ser Ser Tyr Leu Trp Arg His Val Val
    50                  55                  60 cca cat att gag cca gta gcg cgg tgt att ata cca gat ctt att ggt       240
Pro His Ile Glu Pro Val Ala Arg Cys Ile Ile Pro Asp Leu Ile Gly
65                  70                  75                  80 atg ggc aaa tca ggc aaa tct ggt aat ggt tct tat agg tta ctt gat       288
Met Gly Lys Ser Gly Lys Ser Gly Asn Gly Ser Tyr Arg Leu Leu Asp
                85                  90                  95 cat tac aaa tat ctt act gca tgg ttt gaa ctt ctt aat tta cca aag       336
His Tyr Lys Tyr Leu Thr Ala Trp Phe Glu Leu Leu Asn Leu Pro Lys
            100                 105                 110 aag atc att ttt gtc ggc cat gat tgg ggt gct tgt ttg gca ttt cat       384
Lys Ile Ile Phe Val Gly His Asp Trp Gly Ala Cys Leu Ala Phe His
        115                 120                 125 tat agc tat gag cat caa gat aag atc aaa gca ata gtt cac gct gaa       432
Tyr Ser Tyr Glu His Gln Asp Lys Ile Lys Ala Ile Val His Ala Glu
    130                 135                 140 agt gta gta gat gtg att gaa tca tgg gat gaa tgg cct gat att gaa       480
Ser Val Val Asp Val Ile Glu Ser Trp Asp Glu Trp Pro Asp Ile Glu
145                 150                 155                 160 gaa gat att gcg ttg atc aaa tct gaa gaa gga gaa aaa atg gtt ttg       528
Glu Asp Ile Ala Leu Ile Lys Ser Glu Glu Gly Glu Lys Met Val Leu
                165                 170                 175
```

| | |
|---|---|
| gag aat aac ttc ttc gtg gaa acc atg ttg cca tca aaa atc atg aga<br>Glu Asn Asn Phe Phe Val Glu Thr Met Leu Pro Ser Lys Ile Met Arg<br>                  180                        185                      190 | 576 |
| aag tta gaa cca gaa gaa ttt gca gca tat ctt gaa cca ttc aaa gag<br>Lys Leu Glu Pro Glu Glu Phe Ala Ala Tyr Leu Glu Pro Phe Lys Glu<br>        195                        200                        205 | 624 |
| aaa ggt gaa gtt cgt cgt cca aca tta tca tgg cct cgt gaa atc ccg<br>Lys Gly Glu Val Arg Arg Pro Thr Leu Ser Trp Pro Arg Glu Ile Pro<br>210                        215                        220 | 672 |
| tta gta aaa ggt ggt aaa cct gac gtt gta caa att gtt agg aat tat<br>Leu Val Lys Gly Gly Lys Pro Asp Val Val Gln Ile Val Arg Asn Tyr<br>225                        230                        235                      240 | 720 |
| aat gct tat cta cgt gca agt gat gat tta cca aaa atg ttt att gaa<br>Asn Ala Tyr Leu Arg Ala Ser Asp Asp Leu Pro Lys Met Phe Ile Glu<br>                  245                        250                        255 | 768 |
| tcg gat cca gga ttc ttt tcc aat gct att gtt gaa ggc gcc aag aag<br>Ser Asp Pro Gly Phe Phe Ser Asn Ala Ile Val Glu Gly Ala Lys Lys<br>        260                        265                        270 | 816 |
| ttt cct aat act gaa ttt gtc aaa gta aaa ggt ctt cat ttt tcg caa<br>Phe Pro Asn Thr Glu Phe Val Lys Val Lys Gly Leu His Phe Ser Gln<br>275                        280                        285 | 864 |
| gaa gat gca cct gat gaa atg gga aaa tat atc aaa tcg ttc gtt gag<br>Glu Asp Ala Pro Asp Glu Met Gly Lys Tyr Ile Lys Ser Phe Val Glu<br>290                        295                        300 | 912 |
| cga gtt ctc aaa aat gaa caa taa<br>Arg Val Leu Lys Asn Glu Gln<br>305                        310 | 936 |

<210> SEQ ID NO 18
<211> LENGTH: 936
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(933)
<223> OTHER INFORMATION: Renilla reniformis humanized type

<400> SEQUENCE: 18

| | |
|---|---|
| atg gct tcc aag gtg tac gac ccc gag caa cgc aaa cgc atg atc act<br>Met Ala Ser Lys Val Tyr Asp Pro Glu Gln Arg Lys Arg Met Ile Thr<br>1                  5                        10                        15 | 48 |
| ggg cct cag tgg tgg gct cgc tgc aag caa atg aac gtg ctg gac tcc<br>Gly Pro Gln Trp Trp Ala Arg Cys Lys Gln Met Asn Val Leu Asp Ser<br>                  20                        25                        30 | 96 |
| ttc atc aac tac tat gat tcc gag aag cac gcc gag aac gcc gtg att<br>Phe Ile Asn Tyr Tyr Asp Ser Glu Lys His Ala Glu Asn Ala Val Ile<br>        35                        40                        45 | 144 |
| ttt ctg cat ggt aac gct gcc tcc agc tac ctg tgg agg cac gtc gtg<br>Phe Leu His Gly Asn Ala Ala Ser Ser Tyr Leu Trp Arg His Val Val<br>50                        55                        60 | 192 |
| cct cac atc gag ccc gtg gct aga tgc atc atc cct gat ctg atc gga<br>Pro His Ile Glu Pro Val Ala Arg Cys Ile Ile Pro Asp Leu Ile Gly<br>65                        70                        75                      80 | 240 |
| atg ggt aag tcc ggc aag agc ggg aat ggc tca tat cgc ctc ctg gat<br>Met Gly Lys Ser Gly Lys Ser Gly Asn Gly Ser Tyr Arg Leu Leu Asp<br>                  85                        90                        95 | 288 |
| cac tac aag tac ctc acc gct tgg ttc gag ctg ctg aac ctt cca aag<br>His Tyr Lys Tyr Leu Thr Ala Trp Phe Glu Leu Leu Asn Leu Pro Lys<br>        100                        105                        110 | 336 |
| aaa atc atc ttt gtg ggc cac gac tgg ggg gct tgt ctg gcc ttt cac<br> | 384 |

```
Lys Ile Ile Phe Val Gly His Asp Trp Gly Ala Cys Leu Ala Phe His
            115                 120                 125 tac tcc tac gag cac caa gac aag atc aag gcc atc gtc cat gct gag    432
Tyr Ser Tyr Glu His Gln Asp Lys Ile Lys Ala Ile Val His Ala Glu
        130                 135                 140 agt gtc gtg gac gtg atc gag tcc tgg gac gag tgg cct gac atc gag    480
Ser Val Val Asp Val Ile Glu Ser Trp Asp Glu Trp Pro Asp Ile Glu
145                 150                 155                 160 gag gat atc gcc ctg atc aag agc gaa gag ggc gag aaa atg gtg ctt    528
Glu Asp Ile Ala Leu Ile Lys Ser Glu Glu Gly Glu Lys Met Val Leu
                165                 170                 175 gag aat aac ttc ttc gtc gag acc atg ctc cca agc aag atc atg cgg    576
Glu Asn Asn Phe Phe Val Glu Thr Met Leu Pro Ser Lys Ile Met Arg
            180                 185                 190 aaa ctg gag cct gag gag ttc gct gcc tac ctg gag cca ttc aag gag    624
Lys Leu Glu Pro Glu Glu Phe Ala Ala Tyr Leu Glu Pro Phe Lys Glu
        195                 200                 205 aag ggc gag gtt aga cgg cct acc ctc tcc tgg cct cgc gag atc cct    672
Lys Gly Glu Val Arg Arg Pro Thr Leu Ser Trp Pro Arg Glu Ile Pro
    210                 215                 220 ctc gtt aag gga ggc aag ccc gac gtc gtc cag att gtc cgc aac tac    720
Leu Val Lys Gly Gly Lys Pro Asp Val Val Gln Ile Val Arg Asn Tyr
225                 230                 235                 240 aac gcc tac ctt cgg gcc agc gac gat ctg cct aag atg ttc atc gag    768
Asn Ala Tyr Leu Arg Ala Ser Asp Asp Leu Pro Lys Met Phe Ile Glu
                245                 250                 255 tcc gac cct ggg ttc ttt tcc aac gct att gtc gag gga gct aag aag    816
Ser Asp Pro Gly Phe Phe Ser Asn Ala Ile Val Glu Gly Ala Lys Lys
            260                 265                 270 ttc cct aac acc gag ttc gtg aag gtg aag ggc ctc cac ttc agc cag    864
Phe Pro Asn Thr Glu Phe Val Lys Val Lys Gly Leu His Phe Ser Gln
        275                 280                 285 gag gac gct cca gat gaa atg ggt aag tac atc aag agc ttc gtg gag    912
Glu Asp Ala Pro Asp Glu Met Gly Lys Tyr Ile Lys Ser Phe Val Glu
    290                 295                 300 cgc gtg ctg aag aac gag cag taa                                    936
Arg Val Leu Lys Asn Glu Gln
305                 310

<210> SEQ ID NO 19
<211> LENGTH: 936
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(933)
<223> OTHER INFORMATION: Renilla reniformis optimized type

<400> SEQUENCE: 19 atg acc agc aag gtc tac gac ccc gag cag aga aag aga atg atc acc     48
Met Thr Ser Lys Val Tyr Asp Pro Glu Gln Arg Lys Arg Met Ile Thr
1               5                   10                  15 ggc ccc cag tgg tgg gcc aga tgc aag cag atg aac gtc ctg gac agc     96
Gly Pro Gln Trp Trp Ala Arg Cys Lys Gln Met Asn Val Leu Asp Ser
            20                  25                  30 ttc atc aac tac tac gac agc gag aag cac gcc gag aac gcc gtc atc    144
Phe Ile Asn Tyr Tyr Asp Ser Glu Lys His Ala Glu Asn Ala Val Ile
        35                  40                  45 ttc ctg cac ggc aac gcc gcc agc agc tac ctg tgg aga cac gtc gtc    192
Phe Leu His Gly Asn Ala Ala Ser Ser Tyr Leu Trp Arg His Val Val
```

|  |  |  |  |  |  |  |  | 50 |  |  |  |  | 55 |  |  |  |  | 60 |  |  |  |  |  |
|---|---|---|---|---|---|---|---|---|---|---|---|---|---|---|---|---|---|---|---|---|---|---|---|

```
ccc cac atc gag ccc gtc gcc aga tgc atc atc ccc gac ctg atc ggc        240
Pro His Ile Glu Pro Val Ala Arg Cys Ile Ile Pro Asp Leu Ile Gly
 65              70                  75                  80 atg ggc aag agc ggc aag agc ggc aac ggc agc tac aga ctg ctg gac        288
Met Gly Lys Ser Gly Lys Ser Gly Asn Gly Ser Tyr Arg Leu Leu Asp
                 85                  90                  95 cac tac aag tac ctg acc gcc tgg ttc gag ctg ctg aac ctg ccc aag        336
His Tyr Lys Tyr Leu Thr Ala Trp Phe Glu Leu Leu Asn Leu Pro Lys
            100                 105                 110 aag atc atc ttc gtc ggc cac gac tgg ggc gcc tgc ctg gcc ttc cac        384
Lys Ile Ile Phe Val Gly His Asp Trp Gly Ala Cys Leu Ala Phe His
                115                 120                 125 tac agc tac gag cac cag gac aag atc aag gcc atc gtc cac gcc gag        432
Tyr Ser Tyr Glu His Gln Asp Lys Ile Lys Ala Ile Val His Ala Glu
130                 135                 140 agc gtc gtc gac gtc atc gag agc tgg gac gag tgg ccc gac atc gag        480
Ser Val Val Asp Val Ile Glu Ser Trp Asp Glu Trp Pro Asp Ile Glu
145                 150                 155                 160 gag gac atc gcc ctg atc aag agc gag gag ggc gag aag atg gtc ctg        528
Glu Asp Ile Ala Leu Ile Lys Ser Glu Glu Gly Glu Lys Met Val Leu
                165                 170                 175 gag aac aac ttc ttc gtc gag acc atg ctg ccc agc aag atc atg aga        576
Glu Asn Asn Phe Phe Val Glu Thr Met Leu Pro Ser Lys Ile Met Arg
            180                 185                 190 aag ctg gag ccc gag gag ttc gcc gcc tac ctg gag ccc ttc aag gag        624
Lys Leu Glu Pro Glu Glu Phe Ala Ala Tyr Leu Glu Pro Phe Lys Glu
                195                 200                 205 aag ggc gag gtc aga aga ccc acc ctg agc tgg ccc aga gag atc ccc        672
Lys Gly Glu Val Arg Arg Pro Thr Leu Ser Trp Pro Arg Glu Ile Pro
210                 215                 220 ctg gtc aag ggc ggc aag ccc gac gtc gtc cag atc gtc aga aac tac        720
Leu Val Lys Gly Gly Lys Pro Asp Val Val Gln Ile Val Arg Asn Tyr
225                 230                 235                 240 aac gcc tac ctg aga gcc agc gac gac ctg ccc aag atg ttc atc gag        768
Asn Ala Tyr Leu Arg Ala Ser Asp Asp Leu Pro Lys Met Phe Ile Glu
                245                 250                 255 agc gac ccc ggc ttc ttc agc aac gcc atc gtc gag ggc gcc aag aag        816
Ser Asp Pro Gly Phe Phe Ser Asn Ala Ile Val Glu Gly Ala Lys Lys
            260                 265                 270 ttc ccc aac acc gag ttc gtc aag gtc aag ggc ctg cac ttc agc cag        864
Phe Pro Asn Thr Glu Phe Val Lys Val Lys Gly Leu His Phe Ser Gln
                275                 280                 285 gag gac gcc ccc gac gag atg ggc aag tac atc aag agc ttc gtc gag        912
Glu Asp Ala Pro Asp Glu Met Gly Lys Tyr Ile Lys Ser Phe Val Glu
290                 295                 300 aga gtc ctg aag aac gag cag taa                                        936
Arg Val Leu Lys Asn Glu Gln
305                 310

<210> SEQ ID NO 20
<211> LENGTH: 18
<212> TYPE: DNA
<213> ORGANISM: Artificial sequence
<220> FEATURE:
<223> OTHER INFORMATION: synthetic DNA

<400> SEQUENCE: 20
aagcttggta ccaccatg                                                     18
```

```
<210> SEQ ID NO 21
<211> LENGTH: 13
<212> TYPE: DNA
<213> ORGANISM: Artificial sequence
<220> FEATURE:
<223> OTHER INFORMATION: synthetic DNA

<400> SEQUENCE: 21
ggatccaacc gcc                                                         13

<210> SEQ ID NO 22
<211> LENGTH: 35
<212> TYPE: DNA
<213> ORGANISM: Artificial sequence
<220> FEATURE:
<223> OTHER INFORMATION: synthetic DNA

<400> SEQUENCE: 22
aagcttggca atccggtact gttggtaaag ccacc                                 35

<210> SEQ ID NO 23
<211> LENGTH: 15
<212> TYPE: DNA
<213> ORGANISM: Artificial sequence
<220> FEATURE:
<223> OTHER INFORMATION: synthetic DNA

<400> SEQUENCE: 23
aagcttggta ccacc                                                       15
```

METHOD FOR SYNTHETIC GENES

REFERENCE TO RELATED APPLICATIONS

This application claims benefit of the priority application, Japanese patent application no. 2014-185629, filed on Sep. 11, 2014.

SEQUENCE LISTING

The instant application contains a sequence listing which has been submitted in ASCII format via EFS-Web and is hereby incorporated by reference in its entirety. Said ASCII copy, created on Aug. 24, 2015 is named G1169_Sequence_Listings_090215.txt and is 93,457 bytes in size.

TECHNICAL FIELD

The present invention relates to a design method for a gene suitable for achieving high-level expression in cells derived from eukaryotes, specifically in mammalian cells, and use thereof.

BACKGROUND OF THE INVENTION

Protein synthesis in living cells is defined by 61 codons (genetic code) encoding 20 amino acids with mRNA transcribed from DNA (gene) as a template. However, it is known that the frequencies of codon usage differ among organisms while amino acids are the same. Thus, all codons are not used equally.

The frequencies of codon usage are strongly biased among organisms. Consequently, when a recombinant protein is expressed using a gene derived from other organisms, it has been attempted to choose the preferred codons for the amino acids used in host cells, chemically synthesize a target gene and optimize the expression level of the protein. For example, the gene that is termed a humanized gene was synthesized by considering codon composition used in human cells to express a heterologous protein in a mammalian cell culture system and gene expression has been studied. The frequency of codon usage has been analyzed in detail (see Codon Usage Database at the Kazusa DNA Res. Inst. (KDRI) website), and the data of codon usage frequency in human cells are disclosed to the public (Table 1). The frequency of codon usage for each amino acid is shown in Table 1, which reveals that codon bias exists in each amino acid. In general, a method for synthesis of humanized genes, which designs a target gene with a GC content of 40% to 50%, and codons with less frequency of use are avoided, has been used for closely match the distribution rate of amino acids and codons shown in Table 1.

TABLE 1

| | Codon frequency in human cells | | | | | | | | | |
|---|---|---|---|---|---|---|---|---|---|---|
| $1^{st}$ base | | | | $2^{nd}$ base | | | | | | $3^{rd}$ base |
| | T | | | C | | A | | G | | |
| T | TTT 0.43 | Phe | TCT 0.18 | Ser | TAT 0.42 | Tyr | TGT 0.42 | Cys | | T |
| | TTC 0.57 | | TCC 0.20 | | TAC 0.58 | | TGC 0.58 | | | C |
| | TTA 0.06 | Leu | TCA 0.15 | | TAA 0.22 | Stop | TGA 0.61 | Stop | | A |
| | TTG 0.12 | | TCG 0.06 | | TAG 0.17 | | TGG 1.00 | Trp | | G |
| C | CTT 0.12 | | CCT 0.29 | Pro | CAT 0.41 | His | CGT 0.09 | Arg | | T |
| | CTC 0.20 | | CCC 0.33 | | CAC 0.59 | | CGC 0.19 | | | C |
| | CTA 0.07 | | CCA 0.27 | | CAA 0.27 | Gln | CGA 0.10 | | | A |
| | CTG 0.43 | | CCG 0.11 | | CAG 0.73 | | CGG 0.19 | | | G |
| A | ATT 0.35 | Ile | ACT 0.23 | Thr | AAT 0.44 | Asn | AGT 0.14 | Ser | | T |
| | ATC 0.52 | | ACC 0.38 | | AAC 0.56 | | AGC 0.25 | | | C |
| | ATA 0.14 | | ACA 0.27 | | AAA 0.40 | Lys | AGA 0.21 | Arg | | A |
| | ATG 1.00 | Met | ACG 0.12 | | AAG 0.60 | | AGG 0.22 | | | G |
| G | GTT 0.17 | Val | GCT 0.26 | Ala | GAT 0.44 | Asp | GGT 0.18 | Gly | | T |
| | GTC 0.25 | | GCC 0.40 | | GAC 0.56 | | GGC 0.33 | | | C |
| | GTA 0.10 | | GCA 0.22 | | GAA 0.41 | Glu | GGA 0.26 | | | A |
| | GTG 0.48 | | GCG 0.10 | | GAG 0.59 | | GGG 0.23 | | | G |

In addition, humanized genes are designed using various software tools, in which not only codon proportions are considered but also deletions of recognition sites for transcription factors, avoidance of palindrome structures, etc. in nucleic acid sequences, deletions of unnecessary restriction enzyme sites and the like are taken into account. However, a synthetic humanized gene could have many different nucleotide sequences depending on combinations even though the gene encodes for the same amino acid sequence. Consequently, it is not assured to provide an improved synthesis method for the production of a gene product, and not always to express it as high expression level when expressed in mammalian cells. It is the current state that humanized genes are thus synthesized.

On the other hand, the genes for aequorin (189 amino acid residues: Patent Document 1) and clytin II (189 amino acid residues: Patent Document 2), which are heterologous proteins derived from coelenterates and low molecular weight photoproteins with molecular weight of about 20,000, were synthesized using a codon with high frequency of use in human cells and examined the expression in an animal cultured cell system derived from mammal. As a result, these genes showed a higher expression activity than wild-type genes, which are described in Patent Documents 1 and 2. However, "a preferred human codon-optimized gene method," which involves synthesizing genes by selecting only preferential codons with high frequency of use, has not yet been recognized to date as a general rule. The reason is considered to be because an extreme codon bias for amino acids in a gene sequence will affect the efficiency of protein production in intracellular protein synthesis, judging from the amount of tRNA species for each amino acid in cells and the difference among biological species. Furthermore, the efficiency of protein expression using synthetic genes prepared by selecting and using only preferential codons with high frequency of use has not been verified either for the proteins with normal molecular weight of 30,000 to 60,000. The GC content of genes in eukaryotes including human is approximately 40%. It is unclear if, in general, synthetic genes with the GC content of not less than 60% and preferentially biased codons in usage frequency are efficiently expressed in eukaryotes.

RELATED ART REFERENCES

[Patent Document 1] International Publication WO 02/88168
[Patent Document 2] Japanese Patent Application Publication No. 2010-172260

DISCLOSURE OF THE INVENTION

Problems to be Solved by the Invention

The inventor has addressed the problem of investigating whether or not a gene design method which involves the feature "only preferential codons with high frequency of use are selected and a GC content of not less than 60% is achieved" can be established as a general rule for preparing proteins with high expression level, and has examined the problem in order to obtain chemically synthesized genes for proteins capable of high-level expression in eukaryotes. The inventor has also addressed the problem whether or not a synthetic gene for the target protein can be efficiently expressed in cells derived from eukaryotes, without considering recognition sites of transcription factors, palindrome structures in nucleic acid sequences, etc. by designing a target protein gene so that only preferential codons with high frequency of use are selected and a GC content of not less than 60% is achieved, and thus investigated the problem by comparing with protein expression using wild-type protein genes.

Means for Solving the Problem

In order to solve the foregoing problem, the inventor chemically synthesized target protein genes by designing a target protein gene so that only preferential codons for 20 amino acids with high frequency of use are selected from the codon usage frequency table (Table 1) in human cells and a GC content of not less than 60% is achieved. Evaluation of the codon-optimize method was performed by using the target protein genes chemically synthesized, expressing the genes in cells and comparing the expression to that using wild-type gene. The target protein genes were evaluated by determining luminescence activity using the model genes of photoproteins (aequorin and clytin II) and various photoenzymes (luciferases), which have lower homology in the primary structure and show different protein structures in high order structure. The results of the evaluation reveal that a gene synthesis method which involves selection of preferred codons with high frequency of use and a GC content over 60% is extremely effective.

The present invention includes the following features.

(1) A method of designing an optimized gene, which comprises altering a nucleotide sequence of a target protein gene, so that only a codon with high frequency of use in human cells is selected and a GC content of not less than 60% is achieved.

(2) The method according to (1) above, wherein the target protein gene is a gene encoding a functional protein or a structural protein.

(3) The method according to (2) above, wherein the target protein gene is a gene encoding a photoprotein or a photoenzyme.

(4) The method according to (3) above, wherein the photoprotein or photoenzyme is selected from aequorin, clytin II, *Gaussia* luciferase, the mutated catalytic protein of *Oplophorus* (shrimp) luciferase, North American firefly luciferase, Japanese firefly *Luciola cruciate* luciferase or *Renilla* luciferase.

(5) The optimized gene synthesized by the method according to (1) or (2) above.

(6) The optimized gene synthesized by the method according to (3) above, encoding a photoprotein or a photoenzyme.

(7) The optimized gene synthesized by the method according to (4) above, encoding aequorin.

(8) The optimized gene synthesized by the method according to (4) above, encoding clytin II.

(9) The optimized gene synthesized by the method according to (4) above, encoding *Gaussia* luciferase.

(10) The optimized gene synthesized by the method according to (4) above, encoding the mutated catalytic protein of *Oplophorus* (shrimp) luciferase.

(11) The optimized gene synthesized by the method according to (4) above, encoding North American firefly luciferase.

(12) The optimized gene synthesized by the method according to (4) above, encoding Japanese firefly *Luciola cruciate* luciferase.

(13) The optimized gene synthesized by the method according to (4) above, encoding *Renilla* luciferase.

(14) An optimized gene comprising the optimized gene according to any one of (5) to (13) above fused with a polynucleotide encoding other protein.

(15) A method of preparing a target protein, which comprises:
preparing a recombinant expression vector, in which the optimized gene synthesized by the method according to (1) or (2) above is used to be placed under the control/regulation of a promoter in a mammalian cell,
introducing the recombinant expression vector into a mammalian cell to produce a recombinant mammalian cell, and,
culturing the recombinant mammalian cell to express the optimized gene.

(16) A method of producing a photoprotein or photoenzyme, which comprises:
preparing a recombinant expression vector, in which the optimized gene synthesized by the method according to (3) above is used to be placed under the control/regulation of a promoter in a mammalian cell,
introducing the recombinant expression vector into a mammalian cell to produce a recombinant mammalian cell, and,
culturing the recombinant mammalian cell to express the optimized gene.

(17) A method of producing a photoprotein or photoenzyme, which comprises preparing a recombinant expression vector, in which any one of the optimized genes synthesized by the method according to (4) above is used to be placed under the control/regulation of a promoter in a mammalian cell, introducing the recombinant expression vector into a mammalian cell to produce a recombinant mammalian cell, and, culturing the recombinant mammalian cell to express the optimized gene.

(18) A method of producing a protein, which comprises preparing a recombinant expression vector, in which the optimized gene synthesized by the method according to (14) above is used to be placed under the control/regulation of a promoter in a mammalian cell, introducing the recombinant expression vector into a mammalian cell to produce a recombinant mammalian cell, and, culturing the recombinant mammalian cell to express the optimized gene.

(19) The method according to any one of (15) to (18), wherein the mammalian cell is a human cell.

(20) A target protein produced by the method according to (15) or (19) above.

(21) A photoprotein or photoenzyme produced by the method according to (16) or (19) above.

(22) A photoprotein or photoenzyme produced by the method according to (17) or (19) above.

(23) A fused target protein produced by the method according to (18) or (19) above.

(24) A recombinant expression vector wherein the optimized gene according to any one of (5) to (14) above is located under the control/regulation of a promoter in a mammalian cell.

(25) A recombinant mammalian cell comprising the optimized gene according to any one of (5) to (14) above.

(26) The recombinant mammalian cell of (25) above, wherein the mammalian cell is a human cell.

(27) A method of increasing the expression level of a target protein, which comprises preparing a recombinant expression vector, in which the optimized gene synthesized by the method according to (1) or (2) above is used to be placed under the control/regulation of a promoter in a mammalian cell, introducing the recombinant expression vector into a mammalian cell to produce a recombinant mammalian cell, and, culturing the recombinant mammalian cell to express the optimized gene.

(28) A method of increasing the expression level of a photoprotein or photoenzyme, which comprises preparing a recombinant expression vector, in which the optimized gene synthesized by the method according to (3) above is used to be placed under the control/regulation of a promoter in a mammalian cell, introducing the recombinant expression vector into a mammalian cell to produce a recombinant mammalian cell, and, culturing the recombinant mammalian cell to express the optimized gene.

(29) A method of increasing the expression level of a photoprotein or photoenzyme, which comprises preparing a recombinant expression vector, in which any one of the optimized genes synthesized by the method according to (4) above is used to be placed under the control/regulation of a promoter in a mammalian cell, introducing the recombinant expression vector into a mammalian cell to produce a recombinant mammalian cell, and, culturing the recombinant mammalian cell to express the optimized gene.

(30) A method of increasing the expression level of a fused target protein, which comprises preparing a recombinant expression vector, in which the optimized gene synthesized by the method according to (14) above is used to be placed under the control/regulation of a promoter in a mammalian cell, introducing the recombinant expression vector into a mammalian cell to produce a recombinant mammalian cell, and, culturing the recombinant mammalian cell to express the optimized gene.

(31) A method of increasing the expression level according to any one of (27) to (30) above, wherein the mammalian cell is a human cell.

(32) A method of increasing the detection sensitivity of a photoprotein or photoenzyme, which comprises preparing a recombinant expression vector, in which the optimized gene synthesized by the method according to (3) above is used to be placed under the control/regulation of a promoter in a mammalian cell, introducing the recombinant expression vector into a mammalian cell to produce a recombinant mammalian cell, and, culturing the recombinant mammalian cell to express the optimized gene.

(33) A method of increasing the detection sensitivity of a photoprotein or photoenzyme, which comprises preparing a recombinant expression vector, in which any one of the optimized genes synthesized by the method according to (4) above is used to be placed under the control/regulation of a promoter in a mammalian cell, introducing the recombinant expression vector into a mammalian cell to produce a recombinant mammalian cell, and, culturing the recombinant mammalian cell to express the optimized gene.

(34) The method of increasing the detection sensitivity according to (32) or (33) above, wherein the mammalian cell is a human cell.

(35) A method of determining a luminescence activity, which comprises contacting the photoprotein or photoenzyme according to (21) or (22) above, or the fused target protein according to (23) above, with luciferin or a luciferin analogue to determine an amount of light generated.

(36) Use of the optimized gene according to any one of (5) to (14) above, the photoprotein or photoenzyme according to (21) or (22) above, or the fused target protein according to (23) above, to enhance the luminescence intensity of luciferin or a luciferin analogue.

(37) A method of assaying the activity of a sequence associated with promoter control, which comprises using as a reporter gene the optimized gene according to any one of (5) to (14) above.

(38) A method of determining changes in intracellular calcium concentration, which comprises expressing the optimized gene according to any one of (5) to (14) above in a mammalian cell to form a photoprotein, a photoenzyme or a fused target protein, contacting the mammalian cell with luciferin or a luciferin analogue, and determining an amount of light generated.

(39) The method of determining changes in intracellular calcium concentration according to (38) above, wherein the mammalian cell is a human cell.

(40) A kit comprising at least one of the optimized gene according to any one of (5) to (14), the recombinant expression vector according to (24) above and the recombinant mammalian cell according to (25) or (26) above, and further comprising luciferin and/or a luciferin analogue.

Effects of the Invention

The present invention provides synthetic genes prepared by designing a target protein gene, so that only preferential codons with high frequency of use in human cells are selected and the GC content of not less than 60% is achieved, as well as a method of designing the synthetic genes, thereby expressing the target protein at a high level. The present invention provides synthetic genes for photoproteins or photoenzymes prepared by designing a gene for a photoprotein or photoenzyme, so that only preferential codons with high frequency of use in human cells are selected and the GC content of not less than 60% is achieved, as well as the method of designing the synthetic gene, resulting in higher expression than wild-type genes to improve the detection sensitivity.

In a specific embodiment of the present invention, photoproteins (aequorin, clytin II) and photoenzymes (*Gaussia* luciferase, the mutated 19 kDa protein of *Oplophorus gracilirostris* luciferase, firefly luciferases (from North American firefly, Japanese firefly *Luciola cruciate*), *Renilla* luciferase) are used for an evaluation system, which results are shown. This luminescence system is chosen as an evaluation system because the activity is assayed by luminescence to allow high sensitivity and it is simpler than other evaluation systems. By using the method of the present invention, an increased expression level of proteins has been confirmed in all of the photoproteins or photoenzymes that have low homology in amino acid sequences and have different high-order structure in proteins. Accordingly, the method of the present invention can be applied to general protein expression, but is not limited only to photoproteins or photoenzymes.

MODE FOR CARRYING OUT THE INVENTION

In an embodiment, the present invention relates to a method of designing optimized genes, which comprises altering a nucleotide sequence of a target protein gene so that only a codon with high frequency of use in human cells is selected and a GC content of not less than 60% is achieved.

In an embodiment of the present invention, the term "only a codon with high frequency of use in human cells is selected and a GC content of not less than 60% of total cells is achieved" is intended to mean that, based on Table 1, codon bases (cytosine, guanine, thymidine and adenine) are altered or mutated and a GC content of not less than 60% is achieved. In another embodiment, the GC content can be varied depending on kind of a target protein by appropriately selecting the content from 60% or more.

The optimized gene of the present invention refers to cDNA in general, including genomic DNA. The optimized gene of the present invention can be chemically synthesized by standard techniques in the art of genetic engineering. Alterations or mutations of nucleotide sequences may be performed by novel nucleic acid synthesis, PCR, site-specific mutagenesis using primers properly designed, or methods known to those skilled in the art of genetic engineering. The terminus of the optimized gene of the present invention may be designed to have an appropriate restriction enzyme sequence(s), or a restriction enzyme sequence(s) may also be used for easier cloning to plasmid vectors, etc.

In an embodiment of the present invention, the target protein gene is intended to mean a polynucleotide encoding a protein to be expressed. The target protein gene is appropriately chosen from, but not particularly limited to, polynucleotides encoding desired proteins, and provided for use. The polynucleotide encoding the target protein gene can be chemically synthesized by known techniques based on its nucleotide sequence information. In an embodiment of the present invention, the target protein gene includes a functional protein and a structural protein. As used herein, the functional protein refers to a protein having functions such as enzymes, antibodies, receptors, hormones, and the like. The functional protein further includes photoproteins or photoenzymes. The structural protein refers to cell constituent proteins including collagen, actin, etc.

In a preferred embodiment of the present invention, the target protein gene is intended to mean a polynucleotide encoding a photoprotein or photoenzyme. The photoprotein or photoenzyme is intended to mean wild-type, recombinant or mutant proteins having a luminescence activity, which use a luminescence substrate (luciferin) including its analogue. Wild-type protein genes can be obtained by chemical synthesis using known techniques in the art of genetic engineering, or may also be chemically synthesized when their amino acid sequences are known.

More preferably, the target protein of the present invention includes (i) aequorin, clytin II, clytin I, mitrocomin, obelin, mnemiopsin (*Mnemiopsis* photoprotein) and berovin, which are calcium-binding photoproteins derived from the coelenterata wherein coelenterazine serves as a luminophore, (ii) *Gaussia* luciferase, *Metridia* luciferase, mutated catalytic protein of *Oplophorus* luciferase, *Renilla* luciferase and *Pleuromamma* luciferase, in which coelenterazine serves as a luminescence substrate, (iii) a luciferase derived from beetles (North American firefly luciferase, Japanese firefly *Luciola cruciate* luciferase, Japanese firefly *Luciola lateralis* luciferase, click beetle luciferase, etc.), in which a firefly luciferin (beetle luciferin) serves as a luminescence substrate, (iv) *Vargula* luciferase in which *Vargula* luciferin serves as a luminescence substrate, (v) dinoflagellate luciferase in which dinoflagellate luciferin serves as a luminescence substrate; and the like.

The optimized gene of the present invention may also be a fused type of the optimized gene encoding the target protein with a polynucleotide encoding other protein. The fused protein bearing the control sequence capable of protein expression and the fused sequence is thus expressed in mammalian cells. Other protein may be either an N-terminal fusion protein or a C-terminal fusion protein.

The polynucleotide encoding other protein which is fused with the optimized gene of the present invention specifically includes, but not particularly limited to, secretory or other control sequences, label sequences (e.g., 6-his tag), target-directed sequences, etc. Proteins other than those include green fluorescent proteins, etc. which act as reporters or other markers.

An embodiment of the present invention is a method of producing a target protein, which comprises preparing a recombinant expression vector, in which the optimized gene synthesized is used to be placed under the control/regulation of a promoter operable in a mammalian cell, introducing the recombinant expression vector into mammalian cells to produce recombinant mammalian cells, and, culturing the recombinant mammalian cells to express the optimized gene.

In another embodiment of the method of producing the target protein of the invention, the target protein may be a photoprotein or a photoenzyme. The photoenzyme includes wild-type, recombinant or mutant enzymes having a luminescence activity, which use a wild-type luminescence substrate (luciferin) or its analogue (luciferin analogue). More preferably, the target protein of the present invention includes (i) aequorin, clytin II, clytin I, mitrocomin, obelin, mnemiopsin (*Mnemiopsis* photoprotein) and berovin, which are calcium-binding photoproteins derived from the coelenterata wherein coelenterazine serves as a luminophore, (ii) *Gaussia* luciferase, *Metridia* luciferase, mutated catalytic protein of *Oplophorus* luciferase, *Renilla* luciferase and *Pleuromamma* luciferase, in which coelenterazine serves as a luminescence substrate, (iii) a luciferase derived from beetles (North American firefly luciferase, Japanese firefly (*Luciola cruciate*) luciferase, Japanese firefly (*Luciola lateralis*) luciferase, click beetle luciferase, etc.), in which a firefly luciferin (beetle luciferin) serves as a luminescence substrate, (iv) *Vargula* luciferase in which *Vargula* luciferin serves as a luminescence substrate, (v) dinoflagellate luciferase in which dinoflagellate luciferin serves as a luminescence substrate; and the like. In a further embodiment of the method of producing the target protein of the invention, the target protein may be a fused target protein. The fused target protein is a fusion protein of the target protein (e.g., a photoenzyme, etc.) with other protein (e.g., a tag, a reporter, a marker, etc.). Other protein may be located either at the N-terminus or at the C-terminus.

The expression vector of the present invention may be any vector available for genetic engineering, and plasmid vectors, viral vectors, cosmid vectors, bacterial artificial chromosomes (BAC), yeast artificial chromosomes (YAC) or other non-plasmid vectors.

The expression vector of the present invention is an expression vector for mammalian cells, which contains a promoter operable in mammalian cells and further contains a replication origin, a transcription initiation site, a protein coding site, a polyadenylation site, a transcription termination site, etc. The expression vector of the present invention also contains one or more antibiotic-resistant markers for selection. The promoter operable in mammalian cells includes, for example, cytomegalovirus (CMV) promoter, thymidine kinase (TK) promoter of herpes simplex virus (HSV), SV40 promoter, etc. The protein coding site in the expression vector of the present invention may also contain a signal peptide or a leader sequence for extracellular secretion of the target protein.

A further embodiment of the present invention provides an expression vector suitable for expressing the optimized gene of the present invention. That is, the expression vector is a recombinant expression vector comprising the optimized gene of the present invention. The recombinant expression vector of the present invention is placed under the control/regulation of the promoter operable in mammalian cells.

The host cell in the present invention may be mammalian cells and includes cells derived from mammalians, for example, CHO cells, NSO cells, BHK cells, HT1080 cells, COS cells, HEK293 cells, HeLa cells, MDCK cells, HepG2 cells, MIN6 cells, INS-E1 cells, and iPS cells, etc. More preferably, the mammalian cells of the invention are human cells, namely, cells that can be isolated from humans.

The expression vector of the present invention can be introduced into mammalian cells by techniques known in the art of genetic engineering, which include, for example, the calcium phosphate method, electroporation, microinjection, the DEAE-dextran method, a method using liposome, lipofection using cationic lipids, etc. Where the vector is cyclic, the vector can be linearized by known techniques to introduce into cells.

A further embodiment of the present invention provides mammalian cells suitable for expressing the optimized gene of the present invention. That is, the cells are mammalian cells containing the optimized gene of the present invention. The recombinant mammalian cells of the present invention are preferably human cells.

In an embodiment of the method of producing the target protein of the present invention, incubation of the recombinant mammalian cells, expression of the target protein and purification of the target protein from the culture can be implemented by those skilled in the art using techniques known in the art of genetic engineering (e.g., Sambrook et al. "Molecular Cloning—A Laboratory Manual, second edition 1989").

A still further embodiment of the present invention provides the target protein, photoprotein, photoenzyme or fused target protein, which is produced by expressing the optimized gene of the present invention. The target protein, photoenzyme or fused target protein of the present invention is obtained by the recombinant mammalian cells with an enhanced expression efficiency. In particular, the photoprotein or photoenzyme has an effect of increasing the detection sensitivity because of an increased level of protein expression. Accordingly, the target protein, photoprotein, photoenzyme or fused target protein of the present invention has an unexpected effect of markedly increased expression level, as compared to the target protein, photoenzyme or fusion protein obtained by a production method using conventional wild-type gene sequences.

An embodiment of the present invention is a method of increasing the expression level of a target protein, which comprises preparing a recombinant expression vector, in which the optimized gene synthesized is used to be placed under the control/regulation of a promoter operable in mammalian cells, introducing the recombinant expression vector into mammalian cells to produce recombinant mammalian cells, and culturing the recombinant mammalian cells to express the optimized gene.

In a further embodiment of the method of increasing the expression level of a target protein of the present invention, the target protein may be a photoprotein or photoenzyme or a fusion protein in which the photoprotein or photoenzyme is fused with other protein (e.g., a tag, a reporter, a marker, etc.). In general, recognition sites of transcription factors in mammalians often have a highly AT-rich sequence; when there is the AT-rich sequence in the sequence of a target protein gene, it is suggested that transcription factors will bind to the sequence to cause reduction in its transcription efficiency. Likewise, an increase in the GC content will result in rare presence of the polyA addition sequence AATAAA. The present invention provides an improved efficiency of expression because the GC content of not less than 60% reduces unwanted transcription factor-like binding sequences to make the expression of the optimized gene easier.

An embodiment of the present invention is a method of increasing the detection sensitivity of a photoprotein or photoenzyme, which comprises preparing a recombinant expression vector, in which the optimized gene synthesized is used to be placed under the control/regulation of a promoter operable in a mammalian cell, introducing the recombinant expression vector into a mammalian cell to produce a recombinant mammalian cell, and, culturing the recombinant mammalian cell to express the optimized gene.

In a further embodiment of the method of increasing the expression level of the target protein of the present invention, the protein may be a fusion protein in which the target protein (e.g., the photoprotein or photoenzyme, etc.) is fused with other protein (e.g., a tag, a reporter, a marker, etc.). The present invention provides an increased detection sensitivity of photoenzymes because the expression level of the protein is increased due to the improved transcription efficiency of the gene and improved stability of mRNA.

An embodiment of the present invention is a method of assaying a luminescence activity, which comprises contacting a photoprotein, photoenzyme or fused target protein for the optimized gene of the present invention with wild-type luciferin or a luciferin analogue, and determining an amount of light generated. The amount of light generated can be determined by any known methods.

An embodiment of the present invention is use of the optimized gene of the present invention, the photoprotein or photoenzyme of the present invention, or the fused target protein of the present invention, to enhance the luminescence intensity of luciferin or a luciferin analogue. Another embodiment of the present invention includes use of the optimized gene of the present invention as a reporter gene.

An embodiment of the present invention is a method of assaying the activity of a sequence associated with promoter control, in which the optimized gene of the present invention is used as a reporter gene. Specifically, the activity of the target promoter or other expression control sequence is assayed by fusing the optimized gene of the present invention with a target promoter or other expression control sequence (e.g., an enhancer) to construct a recombinant expression vector, introducing the vector into mammalian cells and detecting luminescence in the presence of luciferin or luciferin analogues.

An embodiment of the present invention is a method of determining changes in intracellular calcium concentration, which comprises expressing the optimized gene of the present invention in a mammalian cell to form a photoprotein, a photoenzyme or a fused target protein, contacting the mammalian cell with luciferin or a luciferin analogue, and determining an amount of light generated.

A further embodiment of the present invention can be used as a method of determining the capability of a compound to activate, block, inhibit, or antagonize a receptor, such as G-protein coupled receptor or ion channel that, when activated, mediates the changes of intracellular calcium ions. For example, mammalian cells genetically engineered to express a receptor for regulating intracellular calcium are incubated with a test compound, and luciferin or a luciferin analogue is added thereto to assay the intensity of luminescence with a standard luminometer. As used herein, the intensity of luminescence is an indicator of the level of intracellular calcium that is released. The results of the luminescence intensity can be used to directly locate a receptor agonist, a receptor antagonist, etc.

An embodiment of the present invention is a kit comprising at least one of the optimized gene of the present invention, the recombinant expression vector of the present invention and the recombinant mammalian cell of the present invention, and further comprising luciferin and/or a luciferin analogue. The kit of the present invention optionally further includes the photoprotein, photoenzyme or fused target protein of the present invention.

The kit of the present invention can be prepared with conventional materials by conventional methods. The kit of the present invention may further contain, e.g., sample tubes, plates, instructions for the kit user, solutions, buffers, reagents, and samples suitable for standardization or control samples. The kit of the present invention may also be used in a variety of methods including measurements using reporter genes, detection markers using luminescence, etc.

Regardless of their purposes, all of the documents and publications described in the specification are incorporated herein by reference, each in its entirety. Furthermore, the specification incorporates by reference disclosure in the claims, specification, abstract and drawings of Japanese Patent Application No. 2014-185629 (filed on Sep. 11, 2014), based on which the priority of the present application is claimed for.

The SEQ ID Nos. in the sequence list of the specification represent the following sequences, respectively.

[SEQ ID NO: 1] represents the nucleotide sequence of the wild-type aequorin gene. The GenBank® Accession No. is L29571.

[SEQ ID NO: 2] represents the nucleotide sequence of the humanized aequorin gene.

[SEQ ID NO: 3] represents the nucleotide sequence of the optimized aequorin gene.

[SEQ ID NO: 4] represents the nucleotide sequence of the wild-type clytin H gene. The GenBank® Accession No. is AB360785.

[SEQ ID NO: 5] represents the nucleotide sequence of the optimized clytin II gene. The GenBank® Accession No, is HJ241347.

[SEQ ID NO: 6] represents the nucleotide sequence of the wild-type *Gaussia* luciferase gene. The GenBank Accession No. is AY015993.

[SEQ ID NO: 7] represents the nucleotide sequence of the humanized *Gaussia* luciferase gene,

[SEQ ID NO: 8] represents the nucleotide sequence of the optimized *Gaussia* luciferase gene.

[SEQ ID NO: 9] represents the nucleotide sequence of the humanized gene for the mutated catalytic protein of *Oplophorus gracilirostris* luciferase. The GenBank® Accession No. is JQ437370.

[SEQ ID NO: 10] represents the nucleotide sequence of the optimized gene for the mutated catalytic protein of *Oplophorus gracilirostris* luciferase. The GenBank Accession No. is AB823628.

[SEQ ID NO: 11] represents the nucleotide sequence of the wild-type gene for North. American firefly (*Photinus pyralis*) luciferase. The GenBank® Accession No. is M15077.

[SEQ ID NO: 12] represents the nucleotide sequence of the humanized North American firefly (*Photinus pyralis*) luciferase gene. The GenBank® Accession No, is AY733225.

[SEQ ID NO: 13] represents the nucleotide sequence of the optimized North American firefly (*Photinus pyralis*) luciferase gene.

[SEQ ID NO: 14] represents the nucleotide sequence of the wild-type Japanese firefly (*Luciola cruciate*) luciferase gene. The GenBank® Accession No. is M26194.

[SEQ ID NO: 15] represents the nucleotide sequence of the humanized Japanese firefly (*Luciola cruciate*) luciferase gene.

[SEQ ID NO: 16] represents the nucleotide sequence of the optimized Japanese firefly (*Luciola cruciate*) luciferase gene.

[SEQ ID NO: 17] represents the nucleotide sequence of the wild-type *Renilla* luciferase gene. The GenBank® Accession No. is M63501,

[SEQ ID NO: 18] represents the nucleotide sequence of the humanized *Renilla* luciferase gene. The GenBank® Accession No. is AY738226.

[SEQ ID NO: 19] represents the nucleotide sequence of the optimized *Renilla* luciferase gene.

[SEQ ID NO: 20] represents the nucleotide sequence of the DNA fragment (HindIII sequence-Kozak sequence-ATG sequence) used in EXAMPLE 2,

[SEQ ID NO: 21] represents the nucleotide sequence of the DNA fragment (BamHI sequence-Kozak sequence) used in EXAMPLE 2,

[SEQ ID NO: 22] represents the nucleotide sequence of the DNA fragment (HindIII sequence Kozak sequence) used in EXAMPLE 2.

[SEQ ID NO: 23] represents the nucleotide sequence of the DNA fragment (HindIII sequence—Kozak sequence) used in EXAMPLE 2.

EXAMPLES

The present invention is specifically described with reference to EXAMPLES below but not limited thereto.

Example 1: Chemical Synthesis of Optimized
Genes Encoding Model Enzymes for Evaluation
and Evaluation of Gene Compositions Novel optimized genes (opAQ, opCLII, nanoKAZ, opG-Luc, opPyLuc, opLcLuc, opRLuc) were chemically synthesized to design, without altering the wild-type amino acid sequences, so that only codons with high frequency of use in human cells are selected and its GC content became over 60% in photoprotein genes (aequorin: AQ, clytin II: CLII) and luciferase genes (*Gaussia* luciferase: GLuc, two firefly luciferases: PyLuc and LcLuc, mutated 19 kDa protein of *Oplophorus gracilirostris* luciferase: KAZ, *Renilla* luciferase: RLuc) as model proteins shown in Table 2; the synthesis was outsourced (to Operon Biotechnologies Inc.). Wild-type genes (wAQ, wCLII, wGLuc, wPyLuc and wLcLuc) and humanized genes (hAQ, nanoLuc, hGLuc, hPyLuc, hLcLuc and hRL), if necessary, and control genes for expression and activity comparisons were prepared by chemical synthesis or PCR.

The frequencies of codons for photoproteins and photoenzymes in wild-type, humanized and optimized protein genes are summarized in Table 2. It was found that the amino acid compositions of the optimized genes of the invention used for evaluation are clearly different from those of wild-type and humanized genes.

TABLE 2

Comparison of codon frequency of use in wild-type, humanized and optimized genes encoding photoproteins and photoenzymes

| Amino acid | Codon | Codon usage frequency in human cells | Aequorin Wild wAQ | Aequorin Human-ized hAQ | Aequorin Opti-mized opAQ | Clytin II Wild wCL-II | Clytin II Opti-mized opCL-II | Gaussia luciferase Wild wGL | Gaussia luciferase Human-ized hGL | Gaussia luciferase Opti-mized opGL | Mutated catalytic protein of Oplophorus gracilirostris luciferase Human-ized nanoLuc | Mutated catalytic protein of Oplophorus gracilirostris luciferase Opti-mized nanoKAZ | North American firefly (Photinus pyralis) luciferase Wild wPyLuc | North American firefly (Photinus pyralis) luciferase Human-ized hPyLuc | North American firefly (Photinus pyralis) luciferase Opti-mized opPyLuc | Japanese firefly (Luciola cruciata) luciferase Wild wLcLuc | Japanese firefly (Luciola cruciata) luciferase Human-ized hLcLuc | Japanese firefly (Luciola cruciata) luciferase Opti-mized opLcLuc | Renilla luciferase Wild wRL | Renilla luciferase Human-ized hRL | Renilla luciferase Opti-mized opRL |
|---|---|---|---|---|---|---|---|---|---|---|---|---|---|---|---|---|---|---|---|---|---|
| F | TTT | 0.43 | 2 | 3 | 0 | 6 | 0 | 5 | 2 | 0 | 3 | 0 | 18 | 4 | 30 | 18 | 11 | 23 | 11 | 4 | 0 |
|  | TTC | 0.57 | 6 | 5 | 8 | 7 | 13 | 2 | 5 | 7 | 5 | 8 | 12 | 26 | 0 | 5 | 12 | 0 | 5 | 12 | 16 |
| L | TTA | 0.06 | 1 | 0 | 0 | 4 | 0 | 2 | 0 | 0 | 0 | 0 | 11 | 0 | 0 | 17 | 4 | 0 | 8 | 0 | 0 |
|  | TTG | 0.12 | 3 | 2 | 0 | 6 | 0 | 2 | 2 | 0 | 1 | 0 | 14 | 10 | 0 | 9 | 6 | 0 | 4 | 0 | 0 |
| S | TCT | 0.18 | 2 | 1 | 0 | 3 | 1 | 1 | 1 | 0 | 0 | 0 | 9 | 1 | 0 | 13 | 6 | 0 | 5 | 0 | 0 |
|  | TCC | 0.23 | 0 | 2 | 0 | 1 | 0 | 0 | 2 | 0 | 3 | 0 | 7 | 0 | 1 | 2 | 7 | 0 | 1 | 10 | 0 |
|  | TCA | 0.15 | 3 | 0 | 0 | 3 | 1 | 0 | 0 | 0 | 0 | 0 | 2 | 5 | 0 | 5 | 4 | 0 | 6 | 1 | 0 |
|  | TCG | 0.06 | 0 | 0 | 0 | 0 | 0 | 1 | 0 | 0 | 0 | 0 | 5 | 0 | 0 | 1 | 2 | 0 | 4 | 0 | 0 |
| Y | TAT | 0.42 | 2 | 3 | 0 | 2 | 0 | 0 | 0 | 0 | 4 | 0 | 8 | 3 | 0 | 13 | 9 | 0 | 12 | 2 | 0 |
|  | TAC | 0.58 | 5 | 4 | 7 | 2 | 4 | 1 | 0 | 1 | 2 | 6 | 11 | 16 | 19 | 8 | 12 | 21 | 1 | 11 | 13 |
| * (Stop) | TAA | 0.22 | 1 | 1 | 1 | 1 | 1 | 0 | 1 | 1 | 1 | 1 | 1 | 0 | 1 | 0 | 1 | 0 | 1 | 0 | 1 |
|  | TAG | 0.17 | 0 | 0 | 0 | 0 | 0 | 0 | 0 | 0 | 0 | 0 | 0 | 0 | 0 | 0 | 0 | 0 | 0 | 0 | 0 |
| C | TGT | 0.42 | 0 | 1 | 0 | 3 | 0 | 6 | 4 | 0 | 1 | 0 | 2 | 1 | 0 | 7 | 4 | 0 | 3 | 1 | 0 |
|  | TGC | 0.58 | 3 | 2 | 3 | 0 | 3 | 5 | 7 | 11 | 2 | 1 | 1 | 2 | 4 | 1 | 4 | 8 | 0 | 2 | 3 |
| * (Stop) | TGA | 0.61 | 0 | 0 | 0 | 0 | 0 | 0 | 0 | 0 | 0 | 0 | 0 | 0 | 0 | 1 | 0 | 1 | 0 | 0 | 3 |
| W | TGG | 1 | 6 | 6 | 6 | 6 | 6 | 1 | 1 | 1 | 3 | 3 | 8 | 2 | 2 | 1 | 1 | 1 | 8 | 8 | 8 |
| L | CTT | 0.12 | 4 | 1 | 0 | 2 | 0 | 4 | 1 | 0 | 1 | 1 | 8 | 0 | 0 | 12 | 6 | 0 | 8 | 3 | 0 |
|  | CTC | 0.2 | 3 | 3 | 0 | 2 | 0 | 4 | 4 | 0 | 2 | 0 | 5 | 8 | 3 | 2 | 10 | 2 | 1 | 6 | 0 |
|  | CTA | 0.07 | 0 | 0 | 0 | 0 | 0 | 1 | 0 | 0 | 0 | 0 | 5 | 6 | 0 | 4 | 4 | 0 | 1 | 0 | 0 |
|  | CTG | 0.43 | 1 | 6 | 12 | 1 | 14 | 3 | 9 | 16 | 12 | 15 | 9 | 27 | 49 | 5 | 19 | 47 | 0 | 13 | 22 |
| P | CCT | 0.29 | 3 | 2 | 0 | 2 | 0 | 2 | 3 | 0 | 1 | 1 | 8 | 2 | 0 | 10 | 8 | 0 | 5 | 11 | 0 |
|  | CCC | 0.33 | 1 | 2 | 6 | 1 | 7 | 3 | 4 | 9 | 1 | 6 | 7 | 16 | 29 | 2 | 10 | 29 | 0 | 3 | 18 |
|  | CCA | 0.27 | 2 | 2 | 0 | 5 | 0 | 4 | 0 | 0 | 0 | 0 | 7 | 8 | 0 | 13 | 8 | 0 | 11 | 4 | 0 |
|  | CCG | 0.11 | 0 | 0 | 0 | 2 | 0 | 0 | 2 | 0 | 4 | 4 | 7 | 3 | 0 | 4 | 3 | 0 | 2 | 0 | 0 |
| H | CAT | 0.41 | 2 | 2 | 0 | 2 | 5 | 0 | 2 | 0 | 2 | 2 | 8 | 4 | 4 | 5 | 5 | 8 | 9 | 2 | 0 |
|  | CAC | 0.59 | 3 | 3 | 5 | 3 | 0 | 0 | 2 | 2 | 2 | 2 | 6 | 10 | 0 | 3 | 3 | 0 | 1 | 8 | 10 |
| Q | CAA | 0.27 | 5 | 1 | 0 | 2 | 0 | 6 | 1 | 0 | 3 | 3 | 9 | 7 | 14 | 12 | 5 | 13 | 6 | 3 | 0 |
|  | CAG | 0.73 | 0 | 4 | 5 | 3 | 4 | 1 | 6 | 7 | 4 | 7 | 7 | 9 | 16 | 1 | 10 | 0 | 1 | 4 | 7 |
| R | CGT | 0.09 | 0 | 0 | 0 | 2 | 0 | 0 | 2 | 0 | 4 | 0 | 2 | 1 | 0 | 9 | 2 | 13 | 4 | 0 | 0 |
|  | CGC | 0.19 | 0 | 1 | 0 | 0 | 0 | 0 | 0 | 0 | 2 | 0 | 2 | 13 | 0 | 2 | 4 | 0 | 0 | 7 | 7 |
|  | CGA | 0.1 | 2 | 0 | 0 | 0 | 0 | 0 | 3 | 0 | 2 | 0 | 4 | 1 | 14 | 9 | 2 | 0 | 2 | 0 | 0 |
|  | CGG | 0.19 | 0 | 1 | 0 | 0 | 0 | 1 | 0 | 2 | 2 | 0 | 2 | 5 | 0 | 2 | 4 | 0 | 0 | 3 | 0 |
| I | ATT | 0.35 | 5 | 4 | 0 | 3 | 0 | 8 | 2 | 0 | 4 | 4 | 18 | 6 | 0 | 22 | 12 | 0 | 12 | 18 | 0 |
|  | ATC | 0.52 | 6 | 6 | 12 | 7 | 11 | 2 | 10 | 13 | 14 | 18 | 11 | 32 | 38 | 5 | 15 | 33 | 6 | 0 | 21 |
|  | ATA | 0.14 | 1 | 2 | 0 | 1 | 0 | 3 | 1 | 0 | 0 | 0 | 9 | 1 | 0 | 6 | 6 | 0 | 3 | 9 | 0 |
| M | ATG | 1 | 5 | 5 | 5 | 4 | 4 | 3 | 4 | 4 | 2 | 2 | 14 | 14 | 14 | 11 | 11 | 11 | 9 | 9 | 9 |
| T | ACT | 0.23 | 2 | 2 | 5 | 4 | 4 | 4 | 1 | 4 | 3 | 0 | 7 | 2 | 0 | 14 | 9 | 0 | 4 | 1 | 0 |
|  | ACC | 0.38 | 2 | 5 | 9 | 1 | 8 | 1 | 5 | 9 | 3 | 10 | 7 | 19 | 29 | 8 | 13 | 36 | 1 | 4 | 6 |

TABLE 2-continued

Comparison of codon frequency of use in wild-type, humanized and optimized genes encoding photoproteins and photoenzymes

| Amino acid | Codon | Codon usage frequency in human cells | Aequorin | | | Clytin II | | Gaussia luciferase | | | Mutated catalytic protein of Oplophorus gracilirostris luciferase | | North American firefly (Photinus pyralis) luciferase | | | Japanese firefly (Luciola cruciate) luciferase | | | Renilla luciferase | | |
|---|---|---|---|---|---|---|---|---|---|---|---|---|---|---|---|---|---|---|---|---|---|
| | | | Wild wAQ | Human-ized hAQ | Opti-mized opAQ | Wild wCL-II | Opti-mized opCL-II | Wild wGL | Human-ized hGL | Opti-mized opGL | Human-ized nanoLuc | Opti-mized nanoKAZ | Wild wPyLuc | Human-ized hPyLuc | Opti-mized opPyLuc | Wild wLcLuc | Human-ized hLcLuc | Opti-mized opLcLuc | Wild wRL | Human-ized hRL | Opti-mized opRL |
| | ACA | 0.27 | 5 | 3 | 1 | 4 | 0 | 3 | 1 | 0 | 4 | 0 | 9 | 7 | 0 | 14 | 10 | 0 | 1 | 0 | 0 |
| | ACG | 0.12 | 1 | 0 | 0 | 0 | 0 | 0 | 2 | 0 | 1 | 0 | 6 | 1 | 0 | 0 | 4 | 0 | 0 | 0 | 0 |
| N | AAT | 0.44 | 4 | 4 | 0 | 3 | 0 | 3 | 1 | 0 | 2 | 0 | 9 | 2 | 0 | 12 | 9 | 0 | 11 | 2 | 0 |
| | AAC | 0.56 | 4 | 4 | 8 | 5 | 8 | 3 | 5 | 6 | 6 | 8 | 10 | 15 | 19 | 8 | 11 | 20 | 2 | 11 | 13 |
| K | AAA | 0.4 | 11 | 6 | 0 | 13 | 0 | 13 | 5 | 0 | 3 | 0 | 26 | 8 | 0 | 40 | 19 | 0 | 21 | 4 | 0 |
| | AAG | 0.6 | 4 | 9 | 15 | 4 | 17 | 6 | 14 | 19 | 4 | 7 | 14 | 31 | 40 | 3 | 24 | 43 | 6 | 23 | 27 |
| S | AGT | 0.14 | 1 | 1 | 0 | 4 | 0 | 0 | 0 | 1 | 1 | 0 | 5 | 4 | 0 | 7 | 4 | 0 | 2 | 1 | 0 |
| | AGC | 0.25 | 0 | 2 | 6 | 0 | 11 | 1 | 2 | 0 | 2 | 6 | 1 | 22 | 29 | 2 | 7 | 30 | 1 | 7 | 19 |
| R | AGA | 0.21 | 3 | 2 | 6 | 2 | 5 | 2 | 0 | 4 | 0 | 7 | 9 | 0 | 20 | 8 | 6 | 0 | 2 | 2 | 13 |
| | AGG | 0.22 | 0 | 2 | 0 | 1 | 0 | 1 | 1 | 5 | 1 | 0 | 1 | 4 | 0 | 0 | 3 | 21 | 3 | 1 | 0 |
| V | GTT | 0.17 | 2 | 2 | 0 | 5 | 0 | 3 | 1 | 0 | 2 | 0 | 17 | 7 | 0 | 33 | 10 | 0 | 12 | 2 | 0 |
| | GTC | 0.25 | 5 | 2 | 8 | 2 | 1 | 0 | 3 | 11 | 3 | 17 | 9 | 5 | 39 | 4 | 12 | 49 | 2 | 8 | 23 |
| | GTA | 0.1 | 1 | 0 | 0 | 0 | 0 | 4 | 0 | 0 | 4 | 0 | 7 | 5 | 0 | 15 | 6 | 0 | 6 | 0 | 0 |
| | GTG | 0.48 | 2 | 6 | 2 | 6 | 6 | 4 | 7 | 0 | 8 | 0 | 11 | 29 | 5 | 3 | 27 | 6 | 3 | 13 | 19 |
| A | GCT | 0.28 | 8 | 4 | 0 | 1 | 0 | 9 | 3 | 1 | 0 | 0 | 8 | 9 | 0 | 12 | 9 | 0 | 5 | 11 | 0 |
| | GCC | 0.4 | 4 | 8 | 16 | 6 | 12 | 6 | 10 | 17 | 2 | 3 | 13 | 28 | 42 | 6 | 13 | 32 | 3 | 9 | 19 |
| | GCA | 0.22 | 4 | 4 | 0 | 4 | 0 | 3 | 2 | 0 | 0 | 0 | 8 | 4 | 0 | 13 | 7 | 0 | 8 | 0 | 0 |
| | GCG | 0.1 | 0 | 0 | 0 | 1 | 0 | 1 | 2 | 0 | 1 | 0 | 13 | 2 | 0 | 1 | 3 | 0 | 3 | 0 | 0 |
| D | GAT | 0.44 | 15 | 10 | 0 | 12 | 0 | 6 | 3 | 0 | 3 | 0 | 17 | 3 | 0 | 20 | 12 | 0 | 16 | 6 | 0 |
| | GAC | 0.56 | 4 | 9 | 19 | 11 | 23 | 6 | 6 | 12 | 9 | 12 | 14 | 29 | 31 | 5 | 13 | 25 | 1 | 11 | 17 |
| E | GAA | 0.41 | 10 | 6 | 0 | 11 | 0 | 9 | 3 | 0 | 7 | 0 | 23 | 7 | 0 | 33 | 16 | 0 | 25 | 2 | 0 |
| | GAG | 0.59 | 5 | 9 | 15 | 3 | 14 | 3 | 9 | 12 | 1 | 8 | 10 | 26 | 33 | 6 | 23 | 39 | 5 | 28 | 30 |
| G | GGT | 0.18 | 4 | 3 | 0 | 3 | 0 | 5 | 9 | 1 | 3 | 1 | 8 | 8 | 0 | 23 | 8 | 0 | 10 | 3 | 0 |
| | GGC | 0.33 | 0 | 4 | 15 | 5 | 13 | 2 | 9 | 16 | 9 | 19 | 9 | 30 | 45 | 9 | 17 | 51 | 4 | 7 | 17 |
| | GGA | 0.26 | 11 | 4 | 0 | 4 | 0 | 9 | 2 | 0 | 3 | 0 | 19 | 2 | 0 | 18 | 13 | 0 | 3 | 3 | 0 |
| | GGG | 0.23 | 0 | 4 | 0 | 1 | 0 | 1 | 4 | 0 | 5 | 0 | 9 | 6 | 0 | 1 | 13 | 0 | 0 | 4 | 0 |
| | Total | | 190 | 190 | 190 | 190 | 190 | 186 | 186 | 186 | 170 | 170 | 551 | 551 | 551 | 549 | 549 | 549 | 312 | 312 | 312 |

The GC contents of wild-type, humanized and optimized genes encoding photoproteins and photoenzymes were compared and summarized in Table 3. As a result, the GC contents of the wild-type genes showed approximately 36.4% to 44.8% in all of the photoproteins and photoenzymes; the GC contents of the humanized genes showed 50.3% to 58.6% in all of the photoproteins and photoenzymes, whereas the GC contents of the optimized genes showed over 60% in all of the photoproteins and photoenzymes.

TABLE 3

Comparison in GC contents of wild, humanized and optimized genes encoding photoproteins and photoenzymes

| Protein | Gene Type | GC Content |
|---|---|---|
| Aequorin | Wild (wAQ) | 42.6 |
|  | Humanized (hAQ) | 50.4 |
|  | Optimized (opAQ) | 61.4 |
| Clytin II | Wild (wCL-II) | 41.6 |
|  | Optimized (opCL-II) | 61.4 |
| Gaussia luciferase | Wild (wGLuc) | 43.4 |
|  | Humanized (hGLuc) | 58.6 |
|  | Optimized (opGLuc) | 63.8 |
| Mutated 19 kDa protein of Oplophorus gracilirostris luciferase | Humanized (nanoLuc) | 52.7 |
|  | Optimized (nanoKAZ) | 60.6 |
| North American firefly luciferase | Wild (wPyLuc) | 44.8 |
|  | Humanized (hPyLuc) | 58.1 |
|  | Optimized (opPyLuc) | 60.9 |
| Japanese firefly Luciola cruciata luciferase | Wild (wLcLuc) | 37.3 |
|  | Humanized (hLcLuc) | 50.3 |
|  | Optimized (opLcLuc) | 62.8 |
| Renilla luciferase | Wild (wRLuc) | 36.4 |
|  | Humanized (hRLuc) | 55.2 |
|  | Optimized (opRLuc) | 60.3 |

Example 2: Construction of Various Expression Vectors in Cultured Cells (1) Aequorin The HindIII-XbaI fragment of wild-type (SEQ ID NO: 1), humanized (SEQ ID NO: 2) or optimized (SEQ ID NO: 3) gene for aequorin with the restriction enzyme HindIII sequence-Kozak sequence-ATG sequence (AAGCTTGG-TACCACCATG: SEQ ID NO: 20) at the 5' end and with the restriction enzyme site XbaI sequence (TCTAGA) at the 3' end was prepared and inserted into the restriction enzyme HindIII-XbaI site of animal cultured cell expression vector pcDNA3 (manufactured by Invitrogen) to construct pcDNA3-wAQ, pcDNA3-hAQ and pcDNA3-opAQ, respectively.

(2) Clytin II

The HindIII-XbaI fragment of wild-type (SEQ ID NO: 4) or optimized (SEQ ID NO: 5) clytin II gene with the restriction enzyme HindIII sequence-Kozak sequence-ATG sequence (AAGCTTGGTACCACCATG: SEQ ID NO: 20) at the 5' end and with the restriction enzyme XbaI sequence (TCTAGA) at the 3' end was prepared and inserted into the restriction enzyme HindIII-XbaI site of animal cultured cell expression vector pcDNA3 (manufactured by Invitrogen) to construct pcDNA3-wCLII and pcDNA3-opCLII, respectively.

(3) Gaussia Luciferase

The BamHI-XbaI fragment of wild-type (SEQ ID NO: 6), humanized (SEQ ID NO: 7) or optimized (SEQ ID NO: 8) gene for Gaussia luciferase with the restriction enzyme BamHI sequence-Kozak sequence (GGATCCAACCGCC: SEQ ID NO: 21) at the 5' end and with the restriction enzyme XbaI sequence (TCTAGA) at the 3' end was prepared and inserted into the restriction enzyme BamHI-XbaI site of animal cultured cell expression vector pcDNA3 (manufactured by Invitrogen) to construct pcDNA3-wGluc and pcDNA3-opGLuc, respectively.

(4) Mutated Catalytic Protein of Oplophorus gracilirostris Luciferase

The fragment with restriction enzymes EcoRI and XbaI at the 5' and 3' ends of humanized (SEQ ID NO: 9) or optimized (SEQ ID NO: 10) gene for the mutated catalytic protein of Oplophorus gracilirostris luciferase was prepared and inserted into the restriction enzyme EcoRI-XbaI site of animal cultured cell secretion expression vector pcDNA3-GLsp (Biochem. Biopphys. Res. Commun. (2013) 437: 23-28) bearing the secretion signal sequence of Gaussia luciferase to construct pcDNA3-GLsp-nanoLuc and pcDNA3-GLsp-dnKAZ, respectively.

(5) North American Firefly (Photinus pyralis) Luciferase

The HindIII-XbaI fragments of the wild-type (SEQ ID NO: 11) and optimized (SEQ ID NO: 13) North American firefly (Photinus pyralis) luciferase genes with the restriction enzyme HindIII sequence-Kozak sequence (AAGCTTG-GCAATCCGGTACTGTTGGTAAAGCCACC: SEQ ID NO: 22) at the 5' end and the restriction enzyme XbaI sequence (TCTAGA) at the 3' end were prepared and replaced for the North American firefly (Photinus pyralis) luciferase gene, which was inserted into the restriction enzyme HindIII-XbaI site of the humanized (SEQ ID NO: 12) North American firefly (Photinus pyralis) luciferase expression vector pGL4.13[luc2/sv40] (manufactured by Promega Inc.) to construct pJN-wPyLuc-sv and pJN-opPy-Luc-sv, respectively.

(6) Japanese Firefly (Luciola cruciate) Luciferase

The HindIII-XbaI fragments of the wild-type (SEQ ID NO: 14), humanized (SEQ ID NO: 15) and optimized (SEQ ID NO: 16) Japanese firefly (Luciola cruciate) luciferase genes with the restriction enzyme HindIII sequence-Kozak sequence (AAGCTTGGCAATCCGGTACTGTTGG-TAAAGCCACC, SEQ ID NO: 22) at the 5' end and the restriction enzyme XbaI sequence (TCTAGA) at the 3' end were prepared and replaced for the North American firefly (Photinus pyralis) luciferase gene inserted into the restriction enzyme HindIII-XbaI site of the humanized (SEQ ID NO: 12) North American firefly (Photinus pyralis) luciferase expression vector pGL4.13[luc2/sv40] (manufactured by Promega Inc.) to construct pJN-wLcLucsv, pJN-hLcLuc-sv and pJN-opLcLuc-sv, respectively.

(7) Renilla luciferase

The HindIII-XbaI fragment of wild-type (SEQ ID NO: 17), humanized (SEQ ID NO: 18) or optimized (SEQ ID NO: 19) Renilla luciferase gene with the restriction enzyme site HindIII-Kozak sequence (AAGCTTGGTACCACC: SEQ ID NO: 22) at the 5' end and with the restriction enzyme site XbaI sequence (TCTAGA) at the 3' end was prepared and inserted into the restriction enzyme HindIII-XbaI site of animal cultured cell expression vector pcDNA3 (manufactured by Invitrogen) to construct pcDNA3-RL, pcDNA3-hRL and pcDNA3-opRL.

Example 3: Gene Transfer by Transfection (1) Purification of expression plasmid

The following experiment was performed using the recombinant plasmid obtained in EXAMPLE 2. The recombinant plasmid was purified from Escherichia coli JM83 or DH5a using a plasmid purification kit (manufactured by QIAGEN), dissolved in sterile water, which was used for transfection.

(2) Transfection Method

Animal cultured cell line CHO-K1 cells were cultured in Ham's F-12 medium (manufactured by Wako Pure Chemicals) (hereinafter sometimes referred to as Ham's-F12) supplemented with 10% (v/v) fetal bovine serum (manufactured by HyClone or Biowest).

(i) Transfection of the Photoprotein Aequorin or Clytin II Expression Plasmid:

CHO-K1 cells were seeded in a 6-well plate with $1\times10^5$ cells/well/2 mL medium (n=3), and cultured in an incubator at 37° C. in 5% (v/v) $CO_2$. After 24 hours, the purified recombinant plasmid was transfected to CHO-K1 cells using a FuGENE® HD (manufactured by Promega) transfection kit. Specifically, 1 μg of the recombinant plasmid and 3 μL of FuGENE® HD were added to 100 μL of serum-free Ham's-F12 medium, which was allowed to stand at room temperature for 15 minutes. Where an internal standard vector is necessary, 0.1 μg of pGL4.13[luc2/sv40] (manufactured by Promega) was used. A solution of DNA-FuGENE® complex was added to cells in 6 wells, After incubation for 24 hours, luminescence activity was determined using cell extracts.

(ii) Transfection of Expression Plasmid for Luciferases Including *Gaussia* Luciferase, Mutated Catalytic Protein of *Oplophorus gracilirostris* Luciferase, Firefly Luciferase and *Renilia* Luciferase:

CHO-K1 cells were seeded in a 24-well plate with $1\times10^5$ cells/well/0.5 mL medium (n=4), and cultured in an incubator at 37° C. in 5% (v/v) $CO_2$. After 24 hours, the purified recombinant plasmid was transfected to CHO-K1 cells using a FuGENE® HD (manufactured by Promega) transfection kit. Specifically, 0.5 μg of the recombinant plasmid and 1.5 μL of FuGENE® HD were added to 25 μL of serum-free Ham's-F12 medium, which was allowed to stand at room temperature for 15 minutes. Where an internal standard vector is necessary, 0.05 μg of pGL4.13[luc2/sv40] (manufactured by Promega) or pGL4.75 [hRLuc/CMV] (manufactured by Promega) was added. A solution of DNA-FuGENE® complex was added to cells in 24 wells. After incubation for 24 hours, luminescence activity was determined using the culture medium or cell extracts.

Example 4: Determination of Luminescence Activity (1) Luminescence Assay for the Photoproteins Aequorin and Clytin H The cells expressed apophotoprotein of the photoprotein obtained in EXAMPLE 3 was washed with 3 mL of PBS (manufactured by Wako Pure Chemicals), and 1 mL of PBS was added thereto. The cells were collected with a scraper. After 250 μL of 30 mM Tris-HCl (pH 7.6)-10 mM EDTA was added to 250 μL of the cell collected, the cells were disrupted on ice with an ultrasonic cell disruptor for 5 seconds. To the cell lysate were added 1 μg of coelenterazine (manufactured by JNC Corp.) and 1 μL, of 2-mercaptoethanol (manufactured by Wako Pure Chemicals). The mixture was allowed to stand at 4° C. for over 3 hours to regenerate photoprotein from apophotoprotein. The regenerated solution (10 μL) was injected with 100 μL of 50 mM $CaCl_2$ dissolved in 50 mM Tris-HCl (pH 7.6) to start the luminescence reaction. Luminescence activity was determined using a luminometer (Berthold Technologies: LB960) in 0.1 second intervals for 5 seconds, and expressed as the mean values (n=3) of the maximum intensity of luminescence ($I_{max}$).

(2) Determination of Luminescence Activity of Secretory *Gaussia* Luciferase

Luminescence activity of secreted *Gaussia* luciferase from cells obtained in EXAMPLE 3 was determined using the culture medium and cell extracts. Cell extracts were prepared by washing the expressed cells 3 times with 0.5 mL of PBS, then adding 100 μL of Passive lysis buffer (manufactured by Promega) thereto and shaking the mixture at room temperature for 15 minutes. After diluting to 100-fold with Passive lysis buffer for determination of luminescence activity in the culture medium or cell extracts, 1 μL was added to 50 μL of PBS containing coelenterazine (0.25 μg) to start the luminescence reaction. Luminescence activity was determined using a luminometer (manufactured by Atto: AB2200) in 0.1 second intervals for 5 seconds, and expressed as the mean values (n=4) of the maximum intensity of luminescence ($I_{max}$).

(3) Determination of Luminescence Activity of Mutated Catalytic Protein of Secretory *Oplophorus gracilirostris* Luciferase The culture medium (1 μL) of the mutated catalytic protein of *Oplophorus gracilirostris* luciferase obtained in EXAMPLE 3 was added to 50 μl of PBS containing coelenterazine (0.25 μg) to start the luminescence reaction. Luminescence activity was determined using a luminometer (manufactured by Atto: AB2200) in 0.1 second intervals for 5 seconds in the presence of a 1/100 attenuation filter, and expressed as the mean values (n=4) of the maximum intensity of luminescence ($I_{max}$).

(4) Determination of Luminescence Activity of North American Firefly (*Photinus pyralis*) luciferase and Japanese firefly (*Luciola cruciate*) luciferase Cell extracts from firefly luciferase expressed cells obtained in EXAMPLE 3 were prepared by washing the expressed cells 3 times with 1 mL of PBS, then adding thereto 100 μL of Passive lysis buffer (manufactured by Promega) and shaking the mixture at room temperature for 15 minutes. The resulting cell extract (10 μL) was added to 50 μL of firefly luciferase assay solution (manufactured by Promega) to start the luminescence reaction. Luminescence activity was measured using a luminometer (manufactured by Atto: AB2200) in 0.1 second intervals for 10 seconds in the presence of a 1/100 attenuation filter, and expressed as the mean values (n=4) of the integrated intensity of luminescence (Int.) for 10 seconds.

(5) Determination of Luminescence Activity of *Renilla* Luciferase

Cell extracts from *Renilla* luciferase expressed cells obtained in EXAMPLE 3 were prepared by washing the expressed cells 3 times with 1 mL of PBS, then adding 100 μL of Passive lysis buffer (manufactured by Promega) thereto and shaking the mixture at room temperature for 15 minutes. The resulting cell extract (10 μL) was added to 50 μL of PBS containing coelenterazine (0.25 μg) to start the luminescence reaction. Luminescence activity was measured using a luminometer (manufactured by Atto: AB2200) in 0.1 second intervals for 10 seconds in the presence of a 1/10 attenuation filter, and expressed as the mean values (n=4) of the integrated intensity of luminescence for 10 seconds.

Example 5: Assay Results of Luminescence Activity in CHO-K1 Cells Shown Below (1) Expression of Aequorin The activity of aequorin expressed in cells was determined by the assay method described in EXAMPLE 4 (Table 4). As a result, the luminescence activities of the humanized gene and the optimized gene were 2.7- and 7.9-fold higher, respectively, than that of the wild-type gene.

TABLE 4

| Plasmid | Activity per well ($I_{max}$, ×10$^6$ rlu) | Relative luminescence intensity (%) |
| --- | --- | --- |
| pcDNA3-wAQ (wild-type) | 0.43 | 13.2 |
| pcDNA3-hAQ (humanized) | 1.2 | 37.4 |
| pcDNA3-opAQ (optimized) | 3.3 | 100 |

(2) Expression of Clytin II

The activity of clytin II expressed in cells was determined by the assay method described in EXAMPLE 4 (Table 5). As a result, the luminescence activity of the optimized gene was 11.8-fold higher than that of the wild-type gene.

TABLE 5

| Plasmid | Activity per well ($I_{max}$, ×10$^6$ rlu) | Relative luminescence intensity (%) |
| --- | --- | --- |
| pcDNA3-wCLII (wild-type) | 0.68 | 8.1 |
| pcDNA3-opCLII (optimized) | 8.0 | 100 |

(3) Secretory Expression of *Gaussia* Luciferase

The activity of *Gaussia* luciferase expressed in cells was determined by the assay method described in EXAMPLE 4 (Table 6). As a result, the optimized gene showed 12.6- and 10.8-fold higher activity in the culture medium and in the cells, respectively, than the activity of the wild-type gene in the culture medium and in the cytoplasm.

TABLE 6

| Plasmid | Sample | Activity per well ($I_{max}$, ×10$^6$ rlu) | Relative luminescence intensity (%) |
| --- | --- | --- | --- |
| pcDNA3-wGLuc (wild-type) | Cell extracts | 19.3 | 0.7 |
| | Culture medium | 207.8 | 8.0 |
| pcDNA3-opGLuc (optimized) | Cell extracts | 210.1 | 8.0 |
| | Culture medium | 2,625.8 | 100 |

(4) Secretory Expression of the Mutated Catalytic Protein of *Oplophorus gracilirostris* Luciferase The activity of the mutated catalytic protein of *Oplophorus gracilirostris* luciferase secreted in the culture medium was determined by the assay method described in EXAMPLE 4 (Table 7). As a result, the humanized gene showed the activity of 89% compared to the optimized gene, which was almost the same activity.

TABLE 7

| Plasmid | Activity per well ($I_{max}$, ×10$^6$ rlu) | Relative luminescence intensity (%) |
| --- | --- | --- |
| pcDNA3-GLsp-nanoLuc (humanized) | 139.5 | 89.1 |
| pcDNA3-GLsp-nanoKAZ (optimized) | 156.6 | 100 |

(5) Expression of North American Firefly (*Photinus pyralis*) Luciferase

The activity of North American firefly (*Photinus pyralis*) luciferase in cells was determined by the assay method described in EXAMPLE 4 (Table 8). As a result, the activities of the humanized gene and the optimized gene were 5.2- and 3.4-fold higher, respectively, than that of the wild-type gene.

TABLE 8

| Plasmid | Activity per well (Int., ×10$^6$ rlu) | Relative luminescence intensity (%) |
| --- | --- | --- |
| pJN-wPyLuc-sv40 (wild-type) | 353.5 | 29.1 |
| pGLA.13(luc2/sv40) (humanized) | 1,860.6 | 153 |
| pJN-opPyLuc-sv40 (optimized) | 1,216.2 | 100 |

(6) Expression of Japanese Firefly (*Luciola cruciate*) Luciferase

The activity of Japanese firefly (*Luciola cruciate*) luciferase in cells was determined by the assay method described in EXAMPLE 4 (Table 9). As a result, the activities of the humanized gene and the optimized gene were 320- and 402-fold higher, respectively, than that of the wild-type gene.

TABLE 9

| Plasmid | Activity per well (Int., ×10$^6$ rlu) | Relative luminescence intensity (%) |
| --- | --- | --- |
| pJN-wLcLuc-sv40 (wild-type) | 4.3 | 0.25 |
| pJN-hLcLuc-sv40 (humanized) | 1378.0 | 80.0 |
| pJN-opLcLuc-sv40 (optimized) | 1,722.5 | 100 |

(7) Expression of *Renilla* Luciferase

The activity of *Renilla* luciferase in cells was determined by the assay method described in EXAMPLE 4 (Table 10). As a result, the activities of the humanized gene and the optimized gene were 25.4- and 47.4-fold higher, respectively, than that of the wild-type gene.

TABLE 10

| Plasmid | Activity per well ($I_{max}$, ×10$^6$ rlu) | Relative luminescence intensity (%) |
| --- | --- | --- |
| pcDNA3-wRL (wild-type) | 1.8 | 2.1 |
| pcDNA3-hRL (humanized) | 45.7 | 53.5 |
| pcDNA3-opRL (optimized) | 85.4 | 100 |

The invention claimed is:

1. An isolated polynucleotide comprising the sequence of SEQ ID NO: 8.

2. The polynucleotide of claim 1, further comprising a coding sequence of another protein, wherein the polynucleotide encodes a *Gaussia* luciferase fusion protein.

3. A recombinant expression vector comprising the polynucleotide of claim 1, wherein the sequence of SEQ ID NO: 8 is under the control of a promoter capable of functioning in a mammalian cell.

4. An isolated recombinant mammalian cell comprising the polynucleotide of claim 1.

5. The isolated recombinant mammalian cell of claim 4, wherein the mammalian cell is a human cell.

6. A kit comprising:
a) at least one of (i) an isolated polynucleotide comprising the sequence of SEQ ID NO: 8, (ii) a recombinant expression vector comprising the sequence of SEQ ID NO: 8 under the control of a promoter capable of functioning in a mammalian cell, and (iii) an isolated recombinant mammalian cell comprising a polynucleotide comprising the sequence of SEQ ID NO: 8, and
b) luciferin and/or a luciferin analog.

7. A method of producing a *Gaussia* luciferase protein, comprising:
introducing the recombinant expression vector of claim 3 into a mammalian cell to produce a recombinant mammalian cell, and
culturing the recombinant mammalian cell to produce the *Gaussia* luciferase protein encoded by the sequence of SEQ ID NO: 8.

8. The method of claim 7, wherein the mammalian cell is a human cell.

9. A method of producing a *Gaussia* luciferase fusion protein, comprising:
preparing a recombinant expression vector comprising the polynucleotide of claim 2 under the control of a promoter capable of functioning in a mammalian cell,
introducing the recombinant expression vector into a mammalian cell to produce a recombinant mammalian cell, and
culturing the recombinant mammalian cell to produce the *Gaussia* luciferase fusion protein.

10. A method of determining luminescence activity, comprising:
introducing the recombinant expression vector of claim 3 into a mammalian cell to produce a recombinant mammalian cell,
culturing the recombinant mammalian cell to produce the *Gaussia* luciferase protein encoded by the sequence of SEQ ID NO: 8,
contacting the *Gaussia* luciferase protein with luciferin or a luciferin analogue, and
determining a quantity of light generated by the contacting.

11. The method of claim 10, wherein the mammalian cell is a human cell.

* * * * *